United States Patent [19]

Matsuura et al.

[11] Patent Number: 5,506,110
[45] Date of Patent: Apr. 9, 1996

[54] CARRIER FOR BINDING OF ANTI-PHOSPHOLIPID ANTIBODIES, AND IMMUNOASSAY METHOD USING THE SAME AND A KIT THEREFOR

[75] Inventors: Eiji Matsuura; Yoshiko Igarashi; Hisato Nagae, all of Choshi, Japan

[73] Assignee: Yamasa Shoyu Kabushiki Kaisha, Japan

[21] Appl. No.: 76,365

[22] Filed: Jun. 14, 1993

Related U.S. Application Data

[62] Division of Ser. No. 690,921, filed as PCT/JP90/01355, Oct. 19, 1990, abandoned.

[30] Foreign Application Priority Data

Oct. 19, 1989 [JP] Japan .................................. 1-272536
Mar. 23, 1990 [JP] Japan .................................. 2-074960
Jul. 13, 1990 [JP] Japan .................................. 2-185870

[51] Int. Cl.$^6$ .................................................. G01N 33/564
[52] U.S. Cl. .................... 435/7.94; 435/962; 436/507; 436/815; 436/826; 436/829; 530/380
[58] Field of Search ..................... 436/507, 826, 436/815, 829; 435/7.94, 962; 530/380, 413

[56] References Cited

U.S. PATENT DOCUMENTS

| 4,668,638 | 4/1987 | Janoff et al. ...................... 436/829 |
| 5,344,758 | 9/1994 | Krillis et al. ...................... 435/7.92 |

FOREIGN PATENT DOCUMENTS

| 0306617 | 3/1989 | European Pat. Off. . |
| 90-10227 | 9/1990 | WIPO ..................................... 435/7.94 |

OTHER PUBLICATIONS

Keio J Med, vol. 36, No. 3, pp. 284–297 (1987), Murakami.
Immunological Investigation, vol. 18, 9 & 10, pp. 1121–1127 (1989), Cheng et al.
British Journal of Haematology, vol. 73, No. 4, pp. 506–513 (1989), McNeil et al.
Clin. exp. Immunol., vol. 80, No. 2, pp. 171–176 (1990), Loizou et al.
Thrombosis Research, vol. 52, No. 6, pp. 609–619 (1988), McNeil et al.
The Journal of Rheumatology, vol. 52, No. 1, pp. 80–86 (1988), Hazeltine et al.
J. Amiral et al., Biol. Clin. Hematol., vol. 13, pp. 81–88 (1991).
H. McNeil et al., Proc. Nat'l. Acad. Sci. USA, vol. 87, pp. 4120–4124 (Jun. 1990).
M. Galli et al., The Lancet, vol. 335, pp. 1544–1547 (Jun. 1990).
T. Koike et al., Clin. exp. Immunol., vol. 56, pp. 193–199 (1984).
H. Murakami, Keio J. Med., vol. 36, pp. 284–297 (1987).

*Primary Examiner*—Mary E. Ceperley
*Attorney, Agent, or Firm*—Wenderoth, Lind & Ponack

[57] ABSTRACT

As a carrier for binding of the antiphospholipid antibodies used for immunological diagnosis of antiphospholipid syndrome, a phospholipid-bound carrier treated with purified serum albumin and a surfactant is used. Thus, immunological diagnosis of antiphospholipid syndrome can be made with high accuracy. By using the fraction or protein obtained from animal serum or plasma, having the activity of enhancing the binding ability of the antibodies specifically present in the antiphospholipid syndrome to the phospholipid, immunological diagnosis of antiphospholipid syndrome can also be made more accurately, as compared to known diagnosis.

7 Claims, 29 Drawing Sheets

FIG. I(A)
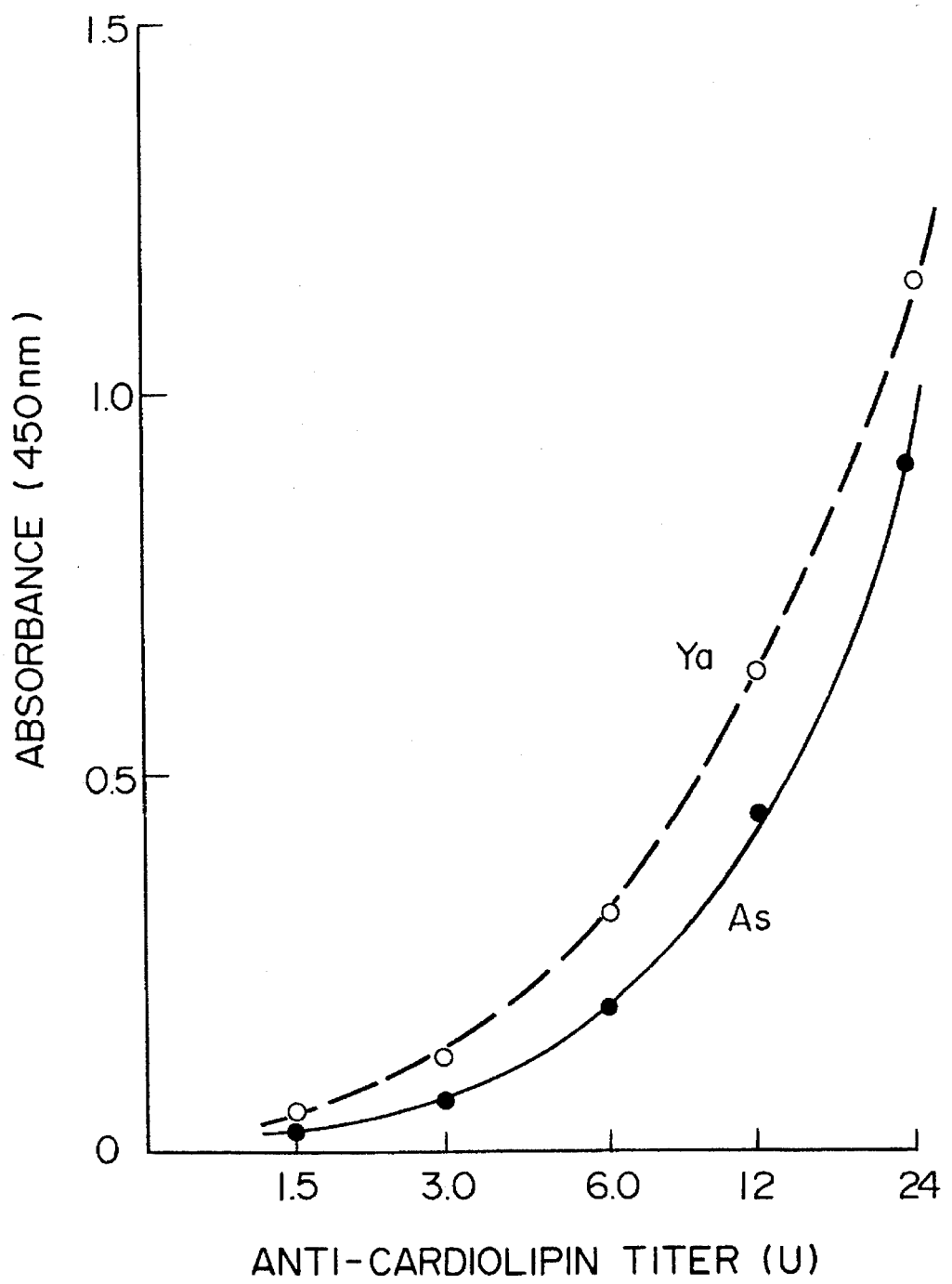

FRACTIONATION OF NORMAL HUMAN SERUM COFACTOR ON DEAE-CELLULOSE COLUMN

ANTI-PHOSPHOLIPID ANTIBODY TITERS OF SERA FROM AUTOIMMUNE DISEASE PATIENTS AND INFECTIOUS DISEASE PATIENTS

FIG. 17

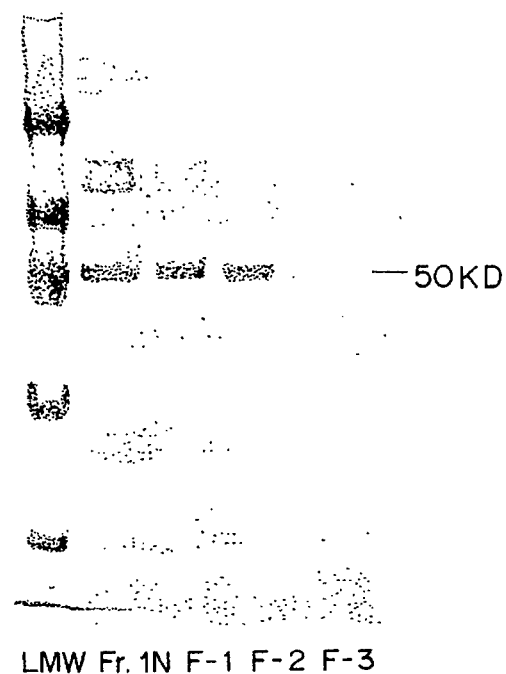

LMW Fr.1N F-1 F-2 F-3

LMW ; LOW MOLECULAR WEIGHT MARKERS

Fr.1N ; CRUDE FRACTION OF ANTICARDIOLIPIN COFACTOR OBTAINED BY THE USE OF DEAE-CELLULOSE DE-52 COLUMN, PROTEIN A-SEPHAROSE COLUMN AND THEN ANTI IgG ANTIBODY-SEPHAROSE CL-4B COLUMN ;

F-1 ; ANTICARDIOLIPIN COFACTOR PURIFIED WITH CARDIOLIPIN LIPOSOMES ;

F-2 ; ANTICARDIOLIPIN COFACTOR PURIFIED WITH LIPOSOMES COMPOSED OF DIPALMITOYLPHOSPHATIDYLCHOLINE (DPPC) AND CARDIOLIPIN (80:20, MOL%) ;

F-3 ; FRACTION PURIFIED WITH LIPOSOMES COMPOSED OF DPPC AND DIPALMITOYLPHOSPHATIDYLETHANOLAMINE (80:20, MOL%) (COULD NOT BE DETECTED)

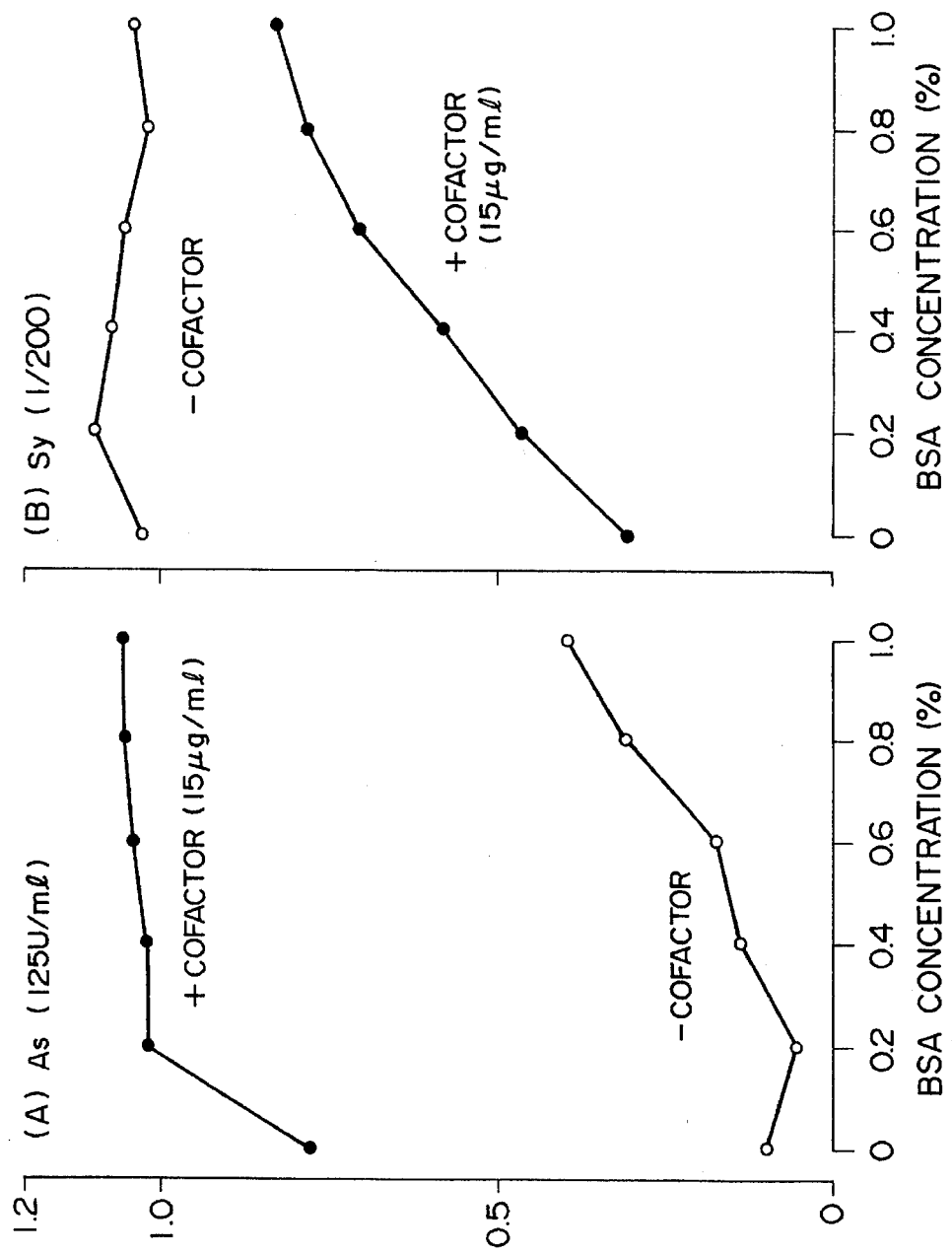

CARRIER FOR BINDING OF ANTI-PHOSPHOLIPID ANTIBODIES, AND IMMUNOASSAY METHOD USING THE SAME AND A KIT THEREFOR

This application is a division of now abandoned application, Ser. No. 07/690,921, filed Jun. 18, 1991, which is the U.S. national stage application of PCT/JP90/01355, filed Oct. 19, 1990.

BACKGROUND OF THE INVENTION

1. Technical Field

The present invention relates to a carrier for binding of antiphospholipid antibodies, an immunoassay method using the same, a kit therefor, and a fraction and a protein obtained from serum or plasma which can be used in the method for immunoassay. In particular, the present invention relates to determination of autoantibodies specifically appeared in patients with antiphospholipid syndrome.

2. Background Art

A living body causes immune response against exogenous foreign matters such as pathogenic viruses, bacteria, fungi, parasites, etc. invaded into a living body, which functions to expel the foreign matters. The phenomenon is generally classified into the following two groups: humoral immunity in which antibodies participate and cellular immunity in which immunocompetent cells directly participate, thereby to expel the foreign matters. In diseases collectively referred to as autoimmune diseases, however, recognition mechanism of self or non-self does not work correctly but humoral or cellular immune response occurs against their own cells or tissues. As a representative clinical case in which antibodies reactive with self components (autoantibodies) appear, there is systemic lupus erythematosus (SLE). It is noted that anti-single stranded DNA antibody (anti-ssDNA), anti-double stranded DNA antibody (anti-dsDNA), anti-Sm antibody, anti-cardiolipin antibody, etc. appeaer in blood of SLE patients. Also rheumatoid factors are found to be noted in those with rheumatoid arthritis (RA); anti-SS-A antibody, anti-SS-B antibody and anti-mitochondrial antibody in those with Sjögren's syndrome (SjS); anti-scl antibody and anti-single stranded DNA antibody in progressive systemic sclerosis (PSS); and anti-RNP antibody in those with mixed connective tissue diseases (MCTD). At this point of time, there are many unclear points regarding relationship between the induction of these antibodies and significance in occurrence of the diseases. However, it is an important means for diagnosis of the diseases and knowledge of change in prognosis to determine the antibodies.

In order to detect these various autoantibodies, immunodiffusion test, counter immunoelectrophoresis, hemagglutination test, radioimmunoassay (RIA), enzyme immunoassay (EIA) and latex agglutination test, etc. have been developed depending on antigenic specificities of antibodies, and biochemical properties and physicochemical properties of antigens.

Turning to a method for determination of the aforesaid anti-cardiolipin antibodies, immunoprecipitation was firstly developed as diagnosis (mass screening) of syphilis in the late 1940's. In the diagnosis using this method, however, there was a problem that sera from patients with systemic lupus erythematosus (SLE) or some autoimmune diseases were shown to be biological false-positive (BFP), in addition to poor sensitivity. In recent years, a high concentration of anti-cardiolipin antibodies was found to be induced in blood of young female patients with lupus-like syndromes showing the symptom of thrombosis in the artery and vein, miscarriage or thrombocytopenia. Great attention has thus been given to clinical significance in diagnosis of these diseases by determining anti-cardiolipin antibodies.

Under such a situation, great expectations have been entertained of highly sensitive and accurate methods, instead of conventional assay such as non-specific determination of lupus anticoagulant or determination of anti-cardiolipin antibodies by immunoprecipitation and hemagglutination in which biological false-positive is noted with high frequence [Proctor, R. R. & Rapaport, S. L., Am. J. Clin. Pathol., 36, 212 (1961); Exner, T. et al., British Haematol., 40, 143 (1978); Margolios, A., Medicine, 40, 145 (1961)]. In 1983, RIA for determination of anti-cardiolipin antibodies was developed by Harris et al. [Harris, E. N., et al., Lancet, 1211–1214 (1983)]. Then, development of EIA was followed by non-competitive method (i.e., a sandwich method) using an antibody labeled with an enzyme, such as alkaline phosphatase. Determination of anti-cardiolipin antibodies by the EIA involved in the system is also quantitative and simple and, seems to be suitable for diagnosis and course observation of collagen diseases such as SLE, etc. In addition, this method is also used for analysis on specificity of anti-cardiolipin antibodies in the field of basic medical science. A strong view has been recently taken that among the region of collagen diseases, especially recurrent abortion would be caused by thrombosis due to induction of antiphospholipid antibodies such as anti-cardiolipin antibodies, etc. (antiphospholipid syndrome). It has thus been expected also in the field of obstetrics and gynecology to determine anti-cardiolipin antibodies.

Various subclasses (i.e., IgG, IgM, IgA, etc.) of anti-cardiolipin antibodies are observed in patients with collagen-diseases and infectious diseases, but IgG or IgM appears frequently in SLE patients.

Further in dsDNA, ssDNA, cardiolipin, phosphatidylserine, phosphatidylinositol, etc. which are seemed to be specific antigens to the respective antibodies specifically raised in sera of patients with antiphospholipid syndrome, similar molecular structures are present at the restricted polar site localizing around phosphodiesters thereof. Discussions have been currently made as to if these antibodies are identical or not.

As stated above, RIA and EIA for determining anti-cardiolipin antibodies have been developed as the assay system for diagnosis of antiphospholipid syndromes including SLE, recurrent abortion, etc. However, these assay methods still encounter the following problems.

That is, where sera of patients with SLE, etc. are provided for the assay, the method using an antigen-bound solid phase carrier sometimes involves difficulty in quantitatively determining antibodies specific to cardiolipin due to the nonspecific adsorption except for using appropriate blocking agent. Where fetal bovine serum (FBS) is conventionally used as a blocking agent, it is impossible to quantitatively determine differentially anti-cardiolipin antibodies derived from SLE and anti-cardiolipin antibodies caused by exogenous origin (i.e., infectious diseases, etc.). Any blocking agents suited for such a purpose have not been found yet.

DISCLOSURE OF THE INVENTION

The present inventors have made extensive investigations to develop suitable carriers for binding of antiphospholipid antibodies which can selectively bind to antiphospholipid antibodies specifically present in antiphospholipid syndrome and a method for determination of anti-cardiolipin antibodies in high accuracy and sensitivity which can be practically applied to a specific diagnosis of the antiphospholipid syndrome. As a result, the foregoing problems could be overcome as follows and the present invention has thus been attained.

That is, the characteristic features of the present invention reside in the following:

(1) A carrier for binding of an antiphospholipid antibody comprising a phospholipid-bound carrier substance treated with purified serum albumin and a surfactant.

(2) A carrier for binding of an antiphospholipid antibody comprising a phospholipid-bound carrier substance treated with purified serum albumin, a surfactant and serum, plasma, a fraction of serum or plasma, or a protein in the fraction.

(3) In an immunoassay method of an antibody specific to antiphospholipid syndrome which comprises contacting a phospholipid-bound carrier for binding of the anti-phospholipid antibody with a sample solution to form an immune complex of the antibody and phospholipid bound to the carrier and detecting the antibody, the method characterized in that the carrier of (1) or (2) described above is used as said carrier for binding of the anti-phospholipid antibody.

(4) In an immunoassay method which comprises:

a step of first antigen-antibody reaction (hereafter sometimes referred to as primary reaction) which comprises contacting a carrier for binding of an anti-phospholipid antibody with a sample solution to form an immune complex (hereafter sometimes referred to as first immune complex) of the anti-phospholipid antibody in said sample solution and phospholipid on the carrier;

a step of second antigen-antibody reaction (hereafter sometimes referred to as secondary reaction) which comprises reacting the first immune complex with a labeled anti-immunoglobulin antibody to form a sandwich immune complex composed of the first immune complex and the labeled anti-immunoglobulin antibody a step of separating a phase containing the sandwich immune complex from a phase containing the substance unbound to the carrier; and, a step of detecting a marker in any one of these phases, the method characterized in that the carrier of (1) or (2) described above is used as the carrier for binding of the anti-phospholipid antibody and that at least the step of first antigen-antibody reaction is carried out in the reaction solution containing serum or plasma, which is derived from the same or akin species of animals as that of the sample solution, or a fraction thereof or a protein in the fraction.

(5) In an immunoassay method which comprises:

a step of first antigen-antibody reaction which comprises contacting a carrier for binding of an anti-phospholipid antibody with a sample solution to form a first immune complex of the anti-phospholipid antibody in said sample solution and phospholipid on the carrier;

a step of second antigen-antibody reaction which comprises reacting the first immune complex with a labeled anti-immunoglobulin antibody to form a sandwich immune complex composed of the first immune complex and the labeled anti-immunoglobulin antibody a step of separating a phase containing the sandwich immune complex from a phase containing the substance unbound to the carrier; and, a step of detecting a marker in any one of these phases, the method characterized in that the carrier for binding of the anti-phospholipid antibody is a carrier obtained by treating a phospholipid-bound carrier with a surfactant and that at least the step of first antigen-antibody reaction is carried out in the reaction solution containing serum or plasma, which is derived from the same or akin species of animals as that of the sample solution, or a fraction thereof or a protein in the fraction.

(6) A kit used for an immunoassay method according to (4) comprising at least the following reagents:

(A) a carrier for binding of the anti-phospholipid antibody of (1) or (2);

(B) a labeled anti-immunoglobulin antibody; and, (C) a sample diluent supplemented with serum or plasma, which is derived from same or akin species of animals as that of the sample solution, or a fraction thereof or a protein in the fraction.

(7) A kit used for an immunoassay method according to (5) comprising at least the following reagents:

(A') a carrier for binding of the anti-phospholipid antibody comprising a phospholipid-bound carrier substance treated with a surfactant;

(B) a labeled anti-immunoglobulin antibody; and, (C) a sample diluent supplemented with serum or plasma, which is derived from same or akin species of animals as that of the sample solution, or a fraction thereof or a protein in the fraction.

(8) A fraction obtained by subjecting serum or plasma to gel filtration, which has a function of enhancing the binding ability of an antiphospholipid specific to antiphospholipid syndrome to phospholipid.

(9) A fraction obtained from serum or plasma, which has a function of enhancing the binding ability of an antiphospholipid specific to anti-phospholipid syndrome to phospholipid and has the following physicochemical properties that:

(a) the fraction contains undialyzable active component(s) by using cellulose membrane having a cut-off molecular weight of 6,000 to 8,000;

(b) the fraction contains active component(s) having molecular weight similar or slightly smaller than that of albumin when fractionated by gel filtration or SDS-polyacrylamide gel electrophoresis;

(c) the fraction contains active component(s) which does not bind to Protein A;

(d) the fraction contains active component(s) which is eluted at similar position of IgG fraction by chromatography using weakly basic anion exchanger containing diethylaminoethyl group; and, (e) the fraction contains active component(s) which is salted out with 30 to 60% saturated ammonium sulfate.

(10) A protein obtained from serum or plasma, which has a function of enhancing the binding ability of an anti-phospholipid antibody specifically present in antiphospholipid syndrome to phospholipid and has the following physicochemical properties that:

(a) its molecular weight is 50,000±2,000 when determined by SDS-polyacrylamide gel electrophoresis and its isoelectric point is 6.60±0.4; and, (b) the protein is capable of binding to phospholipid.

(11) A process for preparing a protein according to (10), which comprises, in isolation and purification of a protein described in (10) from serum collected from normal subjects, a step of purification using liposome comprising phospholipid represented by formula [1] described below, an affinity adsorbent having bound thereto the phospholipid or a liposome containing the phospholipid as one constituent.

(12) In an immunoassay method of an antibody specific to antiphospholipid syndrome which comprises contacting a phospholipid-bound carrier for binding of the anti-phospholipid antibody with a sample solution to form an immune complex of the antibody and phospholipid bound to the carrier to detect the antibody, the method characterized in that upon formation of the immune complex, serum or plasma is present in a high concentration in the reaction solution, or a fraction according to (8) or (9) or a protein according to (10) is present in such a concentration as to correspond to that of serum or plasma in the reaction solution.

(13) In a method for separately detecting an anti-phospholipid antibodies derived from anti-phospholipid syndrome and an anti-phospholipid antibodies derived from infectious diseases which comprises contacting a phospholipid-bound carrier for binding of the anti-phospholipid antibody with a sample solution, the method characterized in that upon contact of the phospholipid-bound carrier for binding of the anti-phospholipid antibody with the sample solution, they are contacted with each other both in the presence of serum or plasma in a high concentration in the reaction solution, or in the presence of a fraction according to (8) or (9) or a protein according to (10) in such a concentration as to correspond to that of serum or plasma in the reaction solution, and in the absence thereof thereby to separately detecting the anti-phospholipid antibodies derived from antiphospholipid syndrome and the anti-phospholipid antibodies derived from infectious diseases.

(14) A kit used for an immunoassay method for determining an antibody specific to antiphospholipid syndrome comprising, at least one of the constituent reagents, a high concentration of serum or plasma, or a suitable concentration of a fraction according to (8) or (9) or a protein according to (10).

BRIEF DESCRIPTION OF THE DRAWINGS

FIG. 5 shows relationship between gel filtration pattern of human sera from normal subjects by HPLC and absorbance (450 nm) as an index of antibody titer in As serum determined by performing the primary reaction under addition of each aliquot of the fraction.

FIG. 17 shows the results obtained by subjecting anticardiolipin cofactor to SDS-polyacrylamide gel electrophoresis.

FIG. 27 shows influence of purified bovine serum albumin on the immunoassay method of the present invention.

BEST MODE FOR CARRYING OUT THE INVENTION

Figure 1B:
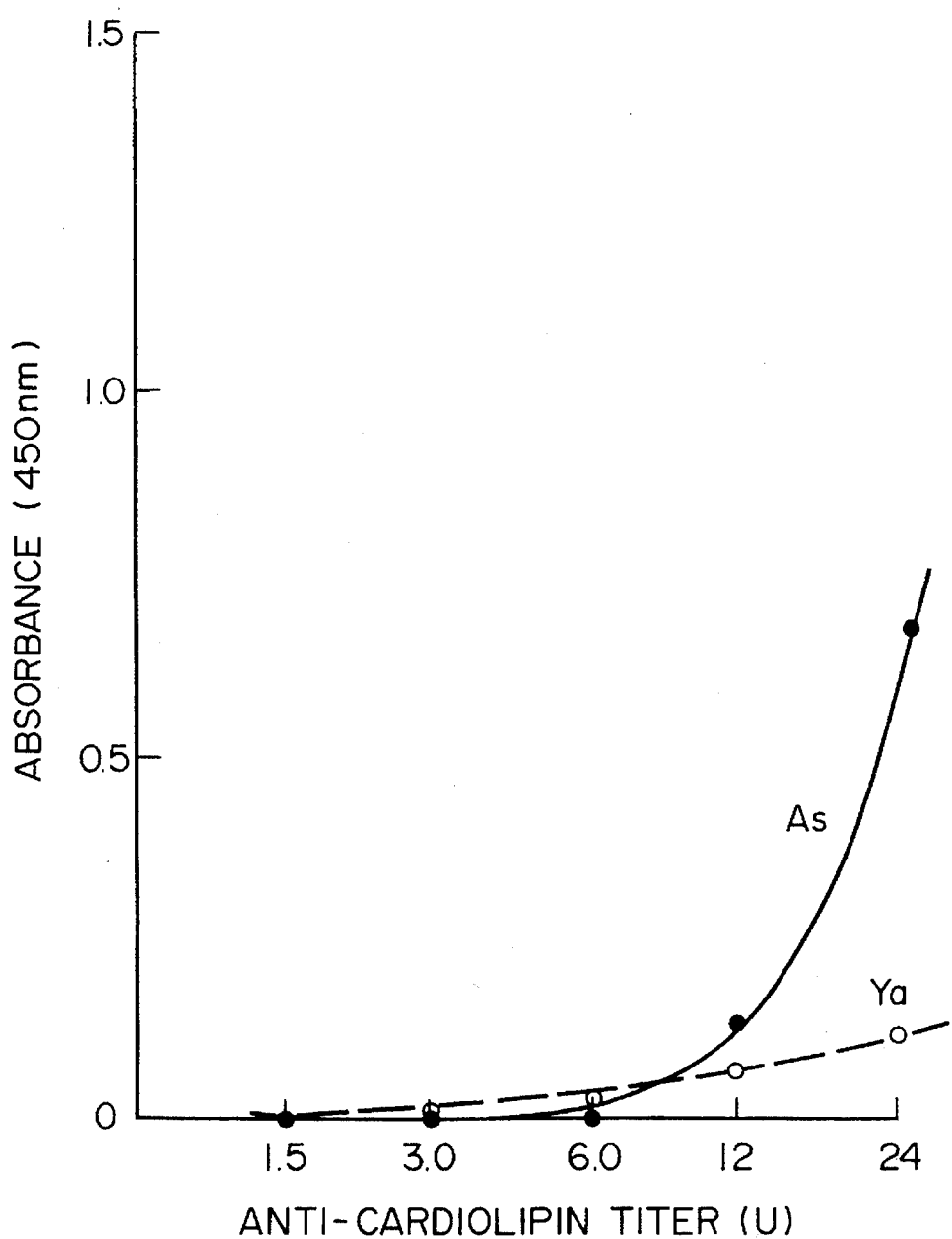
FIG. 1 (A), (B) and (C) indicate the absorbance (450 nm) measured in Reference Example by the prior art process, Experiment showing the effect of the present invention and Example embodying the process of the present invention, respectively, as an index of anti-phospholipid antibody titer in As serum derived from antiphospholipid syndrome and in Ya serum derived from infectious diseases.

Hereafter the present invention is described in detail.

1. Phospholipid

The phospholipid in the present invention may be a phospholipid having an electron donative functional group at the site proximal to its phosphodiester bond. Particularly preferred are glycerophospholipids represented by general formula (I):

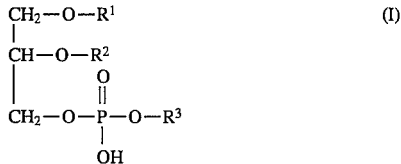

(I)

wherein each of $R^1$ and $R^2$ independently represents an acyl group having an alkyl group or an alkenyl group in the carbon chain thereof, an alkyl group or an alkenyl group; $R^3$ represents a hydrogen atom or $-(CH_2)n-CHR^4-R^5$; $R^4$ represents a hydrogen atom, a hydroxy group, a carboxyl group, a formyl group, a mercapto group or a halogen atom; $R^5$ represents an amino group, a hydroxyalkyl group or a substituent shown by general formula (II):

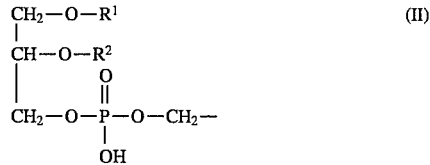

(II)

wherein $R^1$ and $R^2$ have the same significances as described above; or $R^4$ and $R^5$ may be combined together to form a sugar or sugar alcohol residue; and n represents 0 or an integer of 1 to 3. The glycerophospholipids have negative charge and specific examples include cardiolipin, phosphatidylserine, phosphatidylinositol, phosphatidylglycerol and phosphatidic acid.

Inter alia, cardiolipin is preferred. In general, cardiolipin is prepared from the heart of mammal such as bovine, etc., a microorganism such as *Escherichia coli*, etc., with more preference of cardiolipin prepared from the heart of mammal.

The cardiolipin is not limited to its origin composition of fatty acid, degree of purification, etc. The cardiolipin may be in the salt form or in the free form. A solvent in which the cardiolipin is dissolved for binding to a carrier substance is not limited, either, but the degree of purification is preferably comparable to or higher than the reagent class.

2. Carrier substance

Any substance may be used as the carrier substance in the present invention without any particular restriction, so long as it is capable of binding phospholipid and does not inhibit the immune reaction (antigen-antibody reaction) upon determination. Taking easy BF separation (which refers to separation of the labeled immune complex and a free labeled material from each other) into account, it is preferred to use the carrier substance (solid phase) insoluble in the reaction solution.

As materials for the carrier substance insoluble in the reaction solution, there are synthetic organic polymers, for example, poly(vinyl chloride), polystyrene, styrene-divinylbenzene copolymer, styrene-maleic anhydride copolymer, nylon, poly(vinyl alcohol), polyacrylamide, polyacrylonitrile, polypropylene, poly(methyl methacrylate), etc.; polysaccharides such as dextran derivatives (Sephadex, etc.), agarose gel (Sepharose, Biogel, etc.), cellulose (paper disk, filter paper, etc.) and the like; inorganic polymers such as glass, silica gel, silicone, etc. These materials may be introduced with functional groups such as an amino group, an aminoalkyl group, a carboxyl group, an acyl group, a hydroxy group, etc. The materials for the carrier substance are preferably those having a low binding ability to protein. Such materials are exemplified by intact polystyrene, intact poly(vinyl chloride), etc.

The carrier substance insoluble in the reaction solution may be in plate (microtiter plate, disk, etc.), particulate (bead, etc.), tubular (test tube, etc.), fibrous, membrane, fine particulate (latex particles, etc.), capsule, vesicular or liposome-like (multilayer or single layer lipid membrane) shape, etc. Depending upon the method for determination, the carrier of an appropriate shape can be chosen.

3. Carrier for binding of the anti-phospholipid antibodies

The carrier for binding of the anti-phospholipid antibodies in the present invention comprises the aforesaid phospholipid having bound thereto the carrier substance described above. For binding the phospholipid to the carrier substance, there may be adopted known techniques such as physical adsorption, ionic binding, covalent binding, entrapping, etc. (for example, cf., "KOTEIKA KOSO (Immobilized Enzyme)" edited by Ichiro Chibata, published on Mar. 20, 1975 by Kodansha Publishing Co.). Among them, physical adsorption is preferred because of its simplicity. The binding of the phospholipid to the carrier substance may be effected directly or may be performed by inserting other substance between the two substances.

For binding the phospholipid to the carrier substance by physical adsorption, a solution of the phospholipid in an organic solvent (organic solvent such as methanol, ethanol, chloroform, etc. which can dissolve the phospholipid) is generally brought into contact with the carrier substance for an appropriate time period and the organic solvent in the solution is then dried up. Removal of the solvent by drying can be effected by known techniques, e.g., air-drying under reduced pressure, aerial drying, etc. The phospholipid may also be bound to the carrier substance by drying the organic solvent up from the solution of the phospholipid thereby to once adsorb the phospholipid onto the surface of a substance other than the carrier substance, suspending the adsorbed phospholipid in a buffer solution (e.g., phosphate buffered saline of sodium, potassium or sodium-potassium type), etc., contacting the suspension with the carrier substance for an appropriate period of time (e.g., several tens minutes to several hours) at such a temperature condition (e.g., 0° to 50° C.) that does not inhibit the reaction, then removing the solvent by means of suction, decantation, centrifugation, etc.

and, if necessary and desired, drying (drying under reduced pressure, air-drying, etc.).

The carrier for binding of the anti-phospholipid antibodies used in the present invention is preferably treated with a surfactant alone, treated with purified serum albumin and a surfactant in combination, or treated with three of purified serum albumin, a surfactant and serum or plasma as well as fraction thereof or a protein in the fraction (hereafter these materials are sometimes merely referred to as treating materials). The antigen-antibody reaction for forming the first immune complex of the phospholipid bound to the carrier for binding of the anti-phospholipid antibodies and anti-phospholipid antibodies in a sample solution is carried out in the presence of serum or plasma in a high concentration in the reaction solution, or in the presence of the fraction or protein obtained from serum or plasma in the present invention, which will be later described in such a concentration as to correspond to that of serum or plasma in the reaction solution. In this case, the above-described treated carrier for binding of the anti-phospholipid antibodies of the present invention is not necessarily used. Herein, the term "treatment" is used to mean the procedure in which these treating materials can be physically or chemically bound to the carrier for binding of the anti-phospholipid antibodies by acting these materials on the carrier. In more detail, such a treatment can be performed by, after binding the phospholipid to the carrier substance, contacting the phospholipid-bound carrier substance with the respective solutions containing the treating materials sequentially (irrespective of the order) or with the solution containing two or three of these materials, for an appropriate period of time (e.g., several tens minutes to several hours) at such a temperature condition (e.g., 0° to 50° C.) that does not interfere the reaction. In the treatment, a solvent in which these treating materials are dissolved is not particularly limited but there may be generally used buffer solutions (e.g., phosphate buffered saline of sodium, potassium or sodium-potassium type), etc. Such a treatment may also be performed in the presence of sugars (oligosaccharides such as sucrose, etc.; polysaccharides such as dextrin, cyclodextrin, dextran, etc.; monosaccharides and the like) or the like, which are added to the treating solution(s).

By using the thus treated carrier for binding of the anti-phospholipid antibodies, the binding of the carrier of the anti-phospholipid antibodies derived from infectious diseases may be prevented at the step of the first antigen-antibody reaction (primary reaction). By this treatment, additional effects can also be achieved, that is, prevention of non-specific adsorption (prevention of finding of the anti-phospholipid antibodies or the labeled antibodies to the non-binding site of the phospholipid on the carrier substance), potentiated binding ability of the anti-phospholipid antibodies specifically present in the antiphospholipid syndrome to the phospholipid on the carrier substance, stabilization of the phospholipid on the carrier substance, etc.

The purified serum albumin used in the present invention refers to the serum albumin obtained by purifying sera of animal such as bovine, horse, dog, cat, goat, sheep, swine, avian, rabbit, rat, mouse, human, etc., having a higher degree of purity than fraction V (obtained by Cohn's low temperature ethanol fractionation, heat shock method, salting out, etc.) which is adapted for the purpose of the present invention. That is, specific examples of the purified serum albumin which are preferably used include the one purified by subjecting fraction V to a treatment with activated carbon, chromatography (ion exchange chromatography, etc.) or crystallization, and serum albumin having a degree of purity equivalent to the purified fraction V which is purified by other means than above means and has preferably a reduced lipid content.

The serum, plasma, its fraction or the protein in the fraction (hereafter collectively referred to as "blood components of the present invention") is used to mean serum or plasma per se prepared from animal blood by known techniques, the fraction obtained by fractionating serum or plasma, or the protein obtained by further purifying the fraction. The origin is preferably animal belonging to the same species as that of a sample solution to be assayed but may also be animal skin thereto. The blood components of the present invention are basically the same as those supplemented in the primary reaction which will be later described.

In the prior art, phospholipid-bound carriers have been treated with fetal bovine serum, newborn calf serum, bovine serum albumin, a surfactant, etc. According to these known methods, however, it was impossible to prevent the anti-phospholipid antibodies of infectious diseases origin from binding to the carrier for binding of the anti-phospholipid antibodies. In addition, bovine serum albumin conventionally used is fraction V obtained by Cohn's low temperature ethanol fractionation, etc. which is not highly purified.

The surfactants used in the present invention include nonionic, amphoteric, anionic and cationic surfactants. Inter alia, the nonionic surfactant is preferred. Specific examples of the nonionic surfactant are polyoxyethyleneglycolsorbitane alkyl esters (for example, Tween series surfactant, etc.), acylsorbitanes (for example, Span series surfactant, Arlacel series surfactant, etc.), polyoxyethyleneglycol alkylphenyl ethers (for example, Triton series surfactant, etc.), sucrose fatty acid esters, etc.

The carrier for binding of the anti-phospholipid antibodies of the present invention can be used not only for immunoassay but also for various techniques of selectively adsorbing and removing or isolating and purifying the anti-phospholipid antibodies. For example, in plasmaphoresis therapy, the carrier can be used as a selective adsorbent of the anti-phospholipid antibodies (cf., e.g., Japanese Patent Application Laid-Open No. 1-68273). The carrier of the present invention may also be used as an adsorbent for affinity chromatography for isolating and purifying the anti-phospholipid antibodies.

Where the reaction is carried out in the primary reaction described hereinbelow in the presence of the blood components of the present invention, known carriers for binding of the anti-phospholipid antibodies may also be used, instead of using the carrier treated with these treating materials.

4. Antiphospholipid syndrome

The immunoassay using the carrier for binding of the anti-phospholipid antibodies of the present invention can be used for the purpose of diagnosis of antiphospholipid syndrome. The term antiphospholipid syndrome refers to, among autoimmune diseases (systemic lupus erythematosus (SLE), recurrent abortions, etc.), diseases in which anti-phospholipid antibodies appear in body fluids of patients. Such a disease are distinguished from infectious diseases such as tuberculous meningitis, syphilis, etc., in which anti-phospholipid antibodies also appear in body fluids.

The immunoassay method of the present invention is characterized in that the antibodies specific to the antiphospholipid syndrome can be distinguished from and determined differentially from the anti-phospholipid antibodies induced from these infectious diseases.

5. Immunoassay

The immunoassay method of the present invention aims at determining the anti-phospholipid antibodies. As long as the method comprises antigen-antibody reaction using the carrier for binding of the anti-phospholipid antibodies described above and/or reacting the primary reaction in the presence of the blood components of the present invention, the method falls within the present invention, regardless of its procedures, kind of marking labels, labeled substances, carriers, BF separation, etc. Techniques suited for the purpose of the present invention can be appropriately chosen from conventional techniques known to be those for immunoassay.

As the known techniques for immunoassay, the following are known.

When classified in terms of reaction mode of the antigen-antibody reaction, there are known the competitive reaction method and the non-competitive reaction method (immunometric assay). In the present invention, the non-competitive reaction method is preferable.

When classified in terms of detection mode, there are known the non-labeling method (nephelometry, etc.) which directly detects the results of the antigen-antibody reaction and the labeling method for detection using some marker. Either method is applicable to the present invention. Taking sensitivity, etc. into account, the labeling method is particularly preferred. The marker used in the labeling method will be described hereinafter.

The heterogeneous method which requires BF separation and the homogeneous method which requires no BF separation are known. Either method is applicable to the present invention.

For classification by the reaction phase, there are known the liquid phase method in which the overall reaction is carried out in the liquid phase and the solid phase method in which a partner of the immune reaction is immobilized on the solid phase and the reaction is then carried out. In the present invention, the case where the substance soluble in the reaction solution is used as the carrier substance corresponds to the liquid phase method and the case where the substance insoluble in the reaction solution is used as the carrier substance corresponds to the solid phase method.

The relationship between known immunoassay method and the present invention has been described above; general techniques are described in the following publications.

(1) "Radioimmunoassay, second series" edited by Hiroshi Irie (published on May 1, 1979 by Kodansha Publishing Co., Ltd.)

(2) "Enzyme immunoassay" edited by Eiji Ishikawa, et al. (second edition) (published Dec. 15, 1982 by Igaku Shoin Foundation)

(3) Clinical Pathology, Special Extra Issue Number 53 "Immunoassay for clinical examination—Technique and its application" (published in 1983 by Publishing Association of Clinical Pathology)

(4) "Dictionary of Biotechnoloty" (published Oct. 9, 1986 by CMC Co., Ltd.)

(5) "Methods in ENZYMOLOGY", Vol. 70 (Immunochemical techniques (Part A))

(6) "Methods in ENZYMOLOGY", Vol. 73 (Immunochemical techniques (Part B))

(7) "Methods in ENZYMOLOGY", Vol. 74 (Immunochemical techniques (Part C))

(8) "Methods in ENZYMOLOGY", Vol. 84 (Immunochemical techniques (Part D: Selected Immunoassay))

(9) "Methods in ENZYMOLOGY", Vol. 92 (Immunochemical techniques (Part E: Monoclonal Antibodies and General Immunoassay Methods))

[(5) to (9) were published by Academic Press Co., Ltd.]

Hereinafter the immunoassay method of the present invention is concretely described.

5.1 Sample solution

A sample solution in which the presence of the anti-phospholipid antibody or its content is to be determined by the immunoassay method of the present invention (hereafter sometimes simply referred to as the method of the present invention) is a body fluid of animal including human. The term "body fluid" herein refers to blood, serum, ascites, lymph, synovia or a fraction obtained therefrom or other liquid components derived from a living body.

The sample solution may also be diluted with a diluent to an appropriate antibody concentration. Preferred examples of such a diluent include phosphate buffered saline (PBS) of sodium, potassium or sodium-potassium type; Good's buffer (for example, buffer solutions containing buffering agents such as N-2-hydroxyethylpiperazine-N'-2-ethanesulfonic acid (HEPES), N-tris(hydroxymethyl)methyl-2-aminoethanesulfonic acid (TES), 3-(N-morpholino)propanesulfonic acid (MOPS), etc.), glycine buffered saline, veronal buffered saline, Tris buffered saline, etc.

5.2 Step of the first antigen-antibody reaction (primary reaction)

In the present invention, "step of the first antigen-antibody reaction" refers to a step of contacting the carrier for binding of the anti-phospholipid antibody with a sample solution to form a first immune complex of the anti-phospholipid antibody in the sample solution and the phospholipid on the carrier.

The method of the present invention is characterized in that the reaction is carried out using the carrier for binding of the anti-phospholipid antibodies, which is treated with the treating material described above, and/or in the presence of serum or plasma derived from animal of the same species as that from which the sample solution is derived or akin thereto, or in the presence of its fraction or the purified protein in the fraction, in the reaction solution at this step. By such procedures, undesired binding of the infectious disease-induced anti-phospholipid antibodies to the carrier for binding of the anti-phospholipid antibodies can be prevented so that the antibodies specific to the antiphospholipid syndrome can be specifically bound to the carrier.

This step may be performed by contacting body fluids from patients with antiphospholipid syndrome or a standard reagent containing known concentrations of the anti-phospholipid antibodies as a sample solution with the carrier for binding of the anti-phospholipid antibodies for an appropriate period of time (e.g., several tens minutes to several hours) at such a temperature condition that does not inhibit the reaction (e.g., 0° to 50° C.).

In the primary reaction, the purified serum albumin described above may be added and the primary reaction may then be carried out. In this case, the purified serum albumin is used in a concentration of not greater than 5%, preferably not greater than 1%.

The carrier for binding of anti-phospholipid antibody on which first immune complex has been formed is generally separated from the sample solution by an appropriate means for separation, after the step of the primary reaction is completed. The means for separation applicable vary depending on kind of the carrier substance used. Where the carrier substance insoluble in the reaction solution is used, the immune complex may be isolated by known techniques such as suction, decantation, filtration, centrifugation, etc. After the separation, the carrier for binding of the anti-phospholipid antibody may be washed with a buffer solution, etc.

The step of the primary reaction and the step of the secondary reaction may also be performed at the same time.

Alternatively, after the step of the primary reaction, the step of the secondary reaction may be performed without separating the sample solution.

5.3 Fraction and protein

The "serum or plasma derived from animal of the same species as that from which the sample solution is derived" which is used in the step of the primary reaction may be any serum or plasma so long as it's origin is the same as that of a sample solution to be assayed with the anti-phospholipid antibody in its body fluid (including species akin thereto), obtained by known techniques. For example, where human body fluid is to be assayed, human serum or human plasma is used. Serum or plasma from normal subjects is particularly preferred. The fraction thereof is obtained from serum (i.e., human serum, etc.), or plasma (i.e., human plasma, etc.) by known techniques for separation and purification (gel filtration (molecular sieve chromatography); ion exchange chromatography using DEAE-cellulose, etc.; affinity chromatography using Protein A-Sepharose, heparin-Sepharose, cardiolipin-polyacrylamide gel, etc.; affinity adsorption by liposome composed of phospholipids such as cardiolipin, etc.; membrane separation by dialysis, ultrafiltration, etc.; electrophoresis; extraction with a solvent, etc.), which shows the effect of enhancing the binding ability of the antibody specifically present in the anti-phospholipid syndrome to the phospholipid bound to the carrier, by adding the fraction to the reaction solution in the step of the primary reaction according to the method of the present invention.

As the fraction of serum or plasma described above, there is, for example, the fraction obtained by subjecting human serum or plasma to gel filtration using, e.g., Ultrogel ACA-34 (manufactured by LKB Co.) column, and collecting the fraction showing the activity of enhancing the binding ability of the antibodies specifically present in sera from patients with antiphospholipid syndrome to the phospholipid.

Furthermore, there is the fraction having the following physicochemical properties.

(1) The fraction contains undialyzable active component(s) by using a cellulose membrane having a cut-off molecular weight of 6,000 to 8,000;

(2) The fraction contains active components(s) having molecular weight similar or slightly smaller than that of albumin when fractionated by gel filtration or SDS-polyacrylamide gel electrophoresis;

(3) The fraction contains active component(s) which does not bind to Protein A;

(4) The fraction contains active component(s) which is eluted at similar position of IgG fraction by chromatography using weakly basic anion exchanger containing diethylaminoethyl group; and, fraction is eluted around IgG fraction in chromatography using a weakly basic anionic exchanger containing diethylamino group, for example, active component(s) is eluted at similar position as that of IgG (strictly speaking, a slightly later than that of IgG), with eluate, 0.014 M sodium phosphate buffer (pH 7.4) on DEAE-cellulose column chromatography; and, (5) The fraction contains active component(s) which is salted out with 30 to 60% saturated ammonium sulfate.

A concentration of the aforesaid serum, plasma or its fraction or the following protein in the fraction in the antigen-antibody reaction solution described above is not particularly limited so long as the concentration is high enough to achieve the effects of the present invention as described above. It is preferred that such a high concentration of serum or plasma be present in the reaction solution as the concentration of about 200-fold dilution or higher, especially about 40-fold dilution of serum or plasma prepared from blood in a conventional manner or higher; in the case of the fraction and the protein described below, higher than that corresponding to the aforesaid dilution of serum or plasma.

The presence of serum, plasma, its fraction or the protein in the fraction in a high concentration in the primary reaction solution results in potentiating the binding ability of the anti-phospholipid antibodies specifically present in sera from patients with antiphospholipid syndrome to the phospholipid on one hand and on the other hand, inhibiting the undesired reaction between the anti-phospholipid antibodies present in sera from patients with infectious diseases such as tuberculous meningitis, syphilis, etc. and the phospholipid.

The protein which is the active component in the fraction described above can be isolated and purified as a homogeneous protein by the following procedures.

Firstly, serum or plasma from normal subject is subjected to ion exchange column chromatography using, e.g., DEAE-cellulose, etc. to collect the fraction containing the active component. The fractions which have the activity of enhancing the binding ability of the anti-phospholipid antibody specifically present in sera from patients with the antiphospholipid syndrome to the phospholipid is separated.

Next, the thus obtained fraction is subjected to Protein A-Sepharose column chromatography to remove human IgG contained in the fraction. The fraction is further subjected to affinity column chromatography using a column of resin prepared by conjugating anti-human IgG antibody to, e.g., Sepharose CL-4B resin (manufactured by Pharmacia Fine Chemicals) to remove human IgG subclasses non-adsorptive to protein A.

Each fraction obtained after each column chromatography described above may be subjected to dialysis in a conventional manner, if necessary and desired, or may also be appropriately concentrated by ultrafiltration, or salting out with saturated ammonium sulfate.

Then, the purified fraction from which human IgG has been removed is contacted with liposome to adsorb the active component(s) to liposome(s), thereby purifying the active component(s). The liposome(s) used herein are liposomes composed of the phospholipid shown by formula [I] such as cardiolipin, phosphatidylserine, phsophatidylinositol, phosphatidic acid, etc. or a liposome containing the phospholipid as one constituent. The liposomes may be prepared in a conventional manner [Procedures for Immunological Experiment IX, pages 2989–2994, published Dec. 4, 1980 by the Japanese Society of Immunology]. For example, cardiolipin liposomes may be prepared by taking an alcohol solution of cardiolipin in a pear type flask, evaporating to dryness under reduced pressure, adding an appropriate buffer solution to the residue and vigorously stirring the mixture with a vortex mixer.

The fraction containing the active component is added to a buffer solution containing liposomes to absorb the active component to liposomes. Then, a suspension of the active component-absorbed liposomes are subjected to centrifugation. From the resulting supernatant, the purified active component is recovered. The active component may be further purified by subjecting to chromatography such as HPLC, etc.

The thus obtained purified active component shows the following physicochemical properties.

(1) When determined by SDS-polyacrylamide gel electrophoresis, its molecular weight is 50,000±2,000 and its isoelectric point is 6.60±0.4;

(2) The protein is capable of binding to phospholipid. In particular, the active component shows a binding ability specific to the phospholipid such a cardiolipin which has a negative charge. Furthermore, the antibody specifically present in the antiphospholipid syndrome, for example, anti-cardiolipin antibody in patients with autoimmune disease and cardiolipin bound to the carrier are reacted together in dose dependent manner of the active component.

(3) The active component has an inhibitory activity of binding of the reactivity between the anti-phospholipid antibodies induced from infectious diseases such as tuberculous meningitis, syphilis, etc. to the phospholipid.

Based on these properties, it is considered that where the active component described above is added to the reaction system containing cardiolipin bound to the carrier and the antibody specifically present in the antiphospholipid syndrome, the active component would react with cardiolipin bound to the carrier to form the complex and the antibody specific to the antiphospholipid syndrome would bind to the complex.

Since the active component has the properties (2) and (3) described above, the system utilizing the active component(s) can differentially detects the antibodies derived from antiphospholipid syndrome from those derived from infectious diseases, as will be described hereinafter. Also when serum or plasma, or its fraction is present in a high concentration in the reaction solution, the same effects as described above are obtained.

By supplementing the active component protein obtained in the present invention in the first antigen-antibody reaction described above, the antibody specifically present in the sera of patients with the antiphospholipid syndrome can be differentially detected.

5.4 Step of second antigen-antibody reaction (secondary reaction)

The "step of the second antigen-antibody reaction (secondary reaction)" in the present invention refers to a step of reacting the first immune complex with labeled anti-immunoglobulin antibody to form sandwich immune complex, which is composed of the first immune complex and labeled anti-immunoglobulin antibody.

The labeled anti-immunoglobulin antibody used in this step is anti-immunoglobulin antibody labeled with an appropriate marker in response to the detection method described hereinafter.

The anti-immunoglobulin antibody used herein may be any antibody capable of binding of the anti-phospholipid antibody to be assayed or its fragment but is not particularly limited to its origin or process for preparation.

Various subclasses (i.e., IgG, IgM, IgA, etc.) of antiphospholipid antibodies have been observed in body fluid. Therefore, the appropriate anti-immunoglobulin antibody (i.e., anti-IgG antibody, anti-IgM antibody, anti-IgA antibody, etc.), can be chosen depending on its purpose. Where the anti-phospholipid antibody to be assayed is of human origin, needless to say, anti-human immunoglobulin antibody is used.

Such anti-immunoglobulin antibody may be prepared in a conventional manner. It may be obtained by a method which comprises administering to another animal immunoglobulin derived from animal of the same species as that of producing the anti-phospholipid antibody assayed to immunize the animal and isolating and purifying the anti-immunoglobulin antibody from serum of the animal. It may also be obtained by a method which comprises making antibody-forming cells (cf., e.g., spleen cells, lymph node cells, peripheral blood lymphocyte, etc.) of the animal possible to proliferate semi-permanently in a conventional manner such as the hybridoma method, the transformation method (with EB virus, etc.) or the like (cf., e.g., Eur. J. Immunol., 6, 511 (1976)), proliferating the cells in vitro or in vivo and isolating and purifying the antibody from the culture. These anti-immunoglobulin antibodies are commercially available and such antibodies to which one skilled in the art is easily accessible can be used in the method of the present invention.

In addition, the antibody molecule may also be used as the anti-immunoglobulin antibody as it is or may be cleaved by proteinase (for example, papain, pepsin, etc.) to be made antibody fragments [$F(ab')_2$, Fab', etc.), and then used for the present invention.

The marker used to label the anti-immunoglobulin antibody is not particularly limited so long as the marker functions in response to the detection step. The anti-immunoglobulin antibody can be labeled with, for example, a conventional marker such as radioisotopes ($^{125}I$, $^{131}I$, $^{3}H$, $^{14}C$, etc.), enzymes (peroxidase, β-galactosidase, alkaline phosphatase, glucose oxidase, glutamate oxidase, glucose-6-phosphate dehydrogenase, lysozyme, glucoamylase, acetylcholine esterase, maleate dehydrogenase, etc.), ones of ligand-receptor pair existing in a living body (biotin, avidin, streptoavidin, etc.), coenzymes, cofactors (FAD, FMN, ATP, etc.), fluorescent substances (fluorescein isothiocyanate (FITC), europium, phycoerythrin, etc.), luminescent substances (luminol derivatives, etc.), markers for electron spin resonance (ESR) (piperidine-1-N-oxyl compounds, pyrrolidine-1-N-oxyl compounds, etc.), liposomes (containing markers such as enzymes, fluorescent substances, luminescent substances, etc.) and the like (cf., Publications (1), (2) and (4) described above).

Labeling of the anti-immunoglobulin antibody with these markers may also be performed by known techniques. For example, where the radioisotope is used as the marker, the chloramine T method, the enzyme method using lactoperoxidase, etc., the Bolton-Hunter method, etc. may be applied (cf. Publication (1) described above). Where the enzyme is used as the marker, labeling may be performed according to the maleimido crosslinking method (using, e.g., succimidyl 6-maleimido hexanoate (EMCS)), the glutaraldehyde crosslinking method, the periodic acid crosslinking method (Nakane method), the isocyanate crosslinking method [using, e.g., isocyanates (2,4-tolylene diisocyanate, etc.) or isothiocyanates], or the benzoquinone crosslinking method (cf., Publications (1) and (2) supra).

In case that the step of secondary reaction is carried out independently from the step of primary reaction, the reaction can be carried out by contacting the carrier for binding of the anti-phospholipid antibody, on which the first immune complex is formed, with a solution containing labeled anti-immunoglobulin antibody (in a buffer solution, etc.) for an appropriate period of time (for example, several tens minutes to several hours) at such a temperature condition that does not inhibit the reaction (for example, 0° to 50° C.).

Where the secondary reaction is carried out simultaneously with or subsequently to the step of primary reaction without isolating the reaction solution, the labeled anti-immunoglobulin antibody may be present in the reaction solution during or after completion of the primary reaction.

5.5 Step of BF separation

The step of BF separation in the method of the present invention is a step of separating the phase containing the sandwich immune complex formed in the step of secondary reaction from the phase containing the substances unbound to the carrier.

Where the method of the present invention is performed by the homogeneous method, this step is unnecessary but in the case of the heterogeneous method, the BF separation is mandatorily required.

Where the carrier substance insoluble in the reaction solution is used, this step can be performed by known means of separation such as suction, decantation, filtration, centrifugation, etc.

After the operation for separation described above or simultaneously, the carrier may be washed with a buffer solution (PBS, etc.).

5.6 Step of detection

The "step of detection" in the method of the present invention refers to a step for detecting the marker of the labeled anti-immunoglobulin antibody contained in the sandwich immune complex separated in the step of BF separation described above or the marker of the labeled anti-immunoglobulin antibody which did not form the complex, in the case of the heterogeneous method. The detection may be either quantitative or qualitative.

The step of detection may be by any known technique so long as it corresponds to the marker used (cf., Publications (1) to (9) supra). For example, when the radioisotope is used as the marker, its detection is performed using a scintillation counter and when the enzyme is used as the marker, the enzyme activity is detected in a conventional manner used for determination of the activity of the enzyme used.

Hereinafter determination of enzyme activity is described where peroxidase is used as the marker.

The activity of peroxidase may be determined by various methods for detecting transfer of electron when hydrogen peroxide as substrate is decomposed to water. That is, for the determination, there may be utilized known techniques such as determination of change in absorbance based on oxidation of a chromogen, determination of change in redox potential by electrodes, etc. The method using a chromogen is more conventional. As the chromogen, there may be used known compounds, for example, tetraalkylbenzidines (3,3',5,5'-tetramethylbenzidine (TMBZ), etc.), o-phenylenediamine (OPD), 2,2'-azino-di-(3-ethyl)-benzothiazoline sulfonate (6) (ABTS), o-dianisidine, dicarboxidine, 3,3'-diaminobenzidine, etc. (cf., e.g., Japanese National Publication No. 62-502653 (WO86/04610).

Determination of peroxidase activity using a chromogen can be performed by adding a solution containing hydrogen peroxide and a chromogen [preferably a solution in buffer (citrate buffer, tartrate buffer, PBS, etc.)] to one of the phases separated by BF separation, reacting them for an appropriate period of time (for example, for several minutes to several hours) at normal temperature (for example, at room temperature), terminating the reaction by adding a solution for terminating the enzyme reaction (stopping reagent: for example, sulfuric acid) and then measuring the absorbance (in the case of TMBZ, absorbance at 450 nm). Quantitative determination of the anti-phospholipid antibody in the sample solution can be made by comparing the standard curve [showing the relationship between absorbance and a concentration of the antibody (or antibody titer)] determined using a standard reagent containing a known concentration of anti-phospholipid antibody added with serum or plasma derived from animal of the same species as that from which the sample solution is derived or akin thereto, its fraction or the protein in the fraction, with the absorbance measured.

5.7 Differential detection

Differential detection of anti-phospholipid antibodies induced from the antiphospholipid syndrome and from the infectious disease, which are determined in the presence of serum or plasma in a high concentration, or in the presence of its fraction or the active component protein in the fraction in a concentration corresponding to that of serum or plasma, in the reaction solution, is carried out as follows.

That is, the system in which the primary reaction is carried out in the presence of serum, plasma or its fraction or the active component protein in the fraction in a concentration described above in the reaction solution and the system in which the primary reaction is carried out in the absence of these blood components are both performed in the step of the antigen-antibody reaction (primary reaction) described above. When the reactivity of the anti-phospholipid antibody with the phospholipid bound to the carrier is potentiated dependently on these blood components of the present invention being present, it can be judged that the anti-phospholipid antibodies are induced from the antiphospholipid syndrome. Where the reactivity decreases dependently on these blood components of the present invention being present, it can be judged that the anti-phospholipid antibodies are induced from infectious diseases.

6. Kit 6.1 Kit (6)

Kit (6) used for the immunoassay method applied to the method (4) of the present invention comprises constituent reagents of at least (A) to (C) described above.

As the constituent reagent (A): "carrier for binding of the anti-phospholipid antibodies", there are used, among the carriers explained at the section entitled "3. Carrier for binding of the anti-phospholipid antibody", the carrier treated using two of the purified serum albumin and the surfactant, and the carrier treated with three of the purified serum albumin, the surfactant and serum or plasma whose origin is the same species of animal as or akin to that of the sample solution, its fraction or the protein in the fraction. As the constituent reagent (B): "labeled anti-immunoglobulin antibody", there may be used those explained at the section entitled "5.4 Step of second antigen-antibody reaction (secondary reaction)". The constituent reagent (C): "a sample diluent supplemented with serum or plasma, which is derived from the same or akin species of animals as that of the sample solution" in a solution in order to dilute a sample solution to be assayed or standard solution, if necessary; for the same reasons described above, the blood components of the present invention is added thereto.

In addition to the constituent reagents described above, if necessary and desired, the standard reagent or reagents for detecting the marker may also be added to the kit (6) of the present invention. An example of the standard reagent is the one containing the anti-phospholipid antibody in a known concentration and added with the blood components of the present invention, if necessary. In general, the standard reagent is a solution containing the anti-phospholipid antibodies isolated from patients with the anti-phospholipid syndrome which is serially diluted, if necessary, and added with the blood components of the present invention, if necessary, for the reasons described in "5.2 Step of the first antigen-antibody reaction (primary reaction)" stated above. As reagents for detecting the marker, it is preferred to add reagents for determining the enzyme activity, if necessary, where the kit is for the method of enzyme immunoassay, that is, substrate of the enzyme reaction and indicator of the reaction (for example, the chromogen explained in "5.6 Step of detection"). A solution for terminating the enzyme reaction (stopping reagent: for example, a solution containing sulfuric acid) may also be added.

6.2 Kit (7)

The kit (7) for immunoassay method used in the method (5) of the present invention described above comprises the constituent reagents of at least (A') to (C) described above. If necessary and desired, standard reagent and reagents for detecting the marker may be added as in the kit (6).

The constituent reagent (A') is the one treated with the surfactant alone, among the carrier for binding of the anti-phospholipid antibodies explained at the section entitled "3. Carrier for binding of the anti-phospholipid antibody". Other constituent reagents are the same as in Section 6.1 described above.

6.3 Kit (14)

The kit used in the immunoassay method in (12) described above contains, as one of the constituent reagents, serum or plasma or the aforesaid fraction or the protein in the fraction, in appropriate concentration, which is described in detail in the aforementioned explanation of the primary reaction. Any carrier for binding of the anti-phospholipid antibody conventionally used may be used and of course, it may be the carrier for binding of the anti-phospholipid antibody of the present invention described above. Other conventional constituent reagents may also be used as they are.

[EXAMPLES]

Hereafter the present invention is described in more detail by referring to Reference Example and Examples.

Reference Example

Conventional procedures in the prior art and an example for assay by the procedures are given below.

Figure 1C:
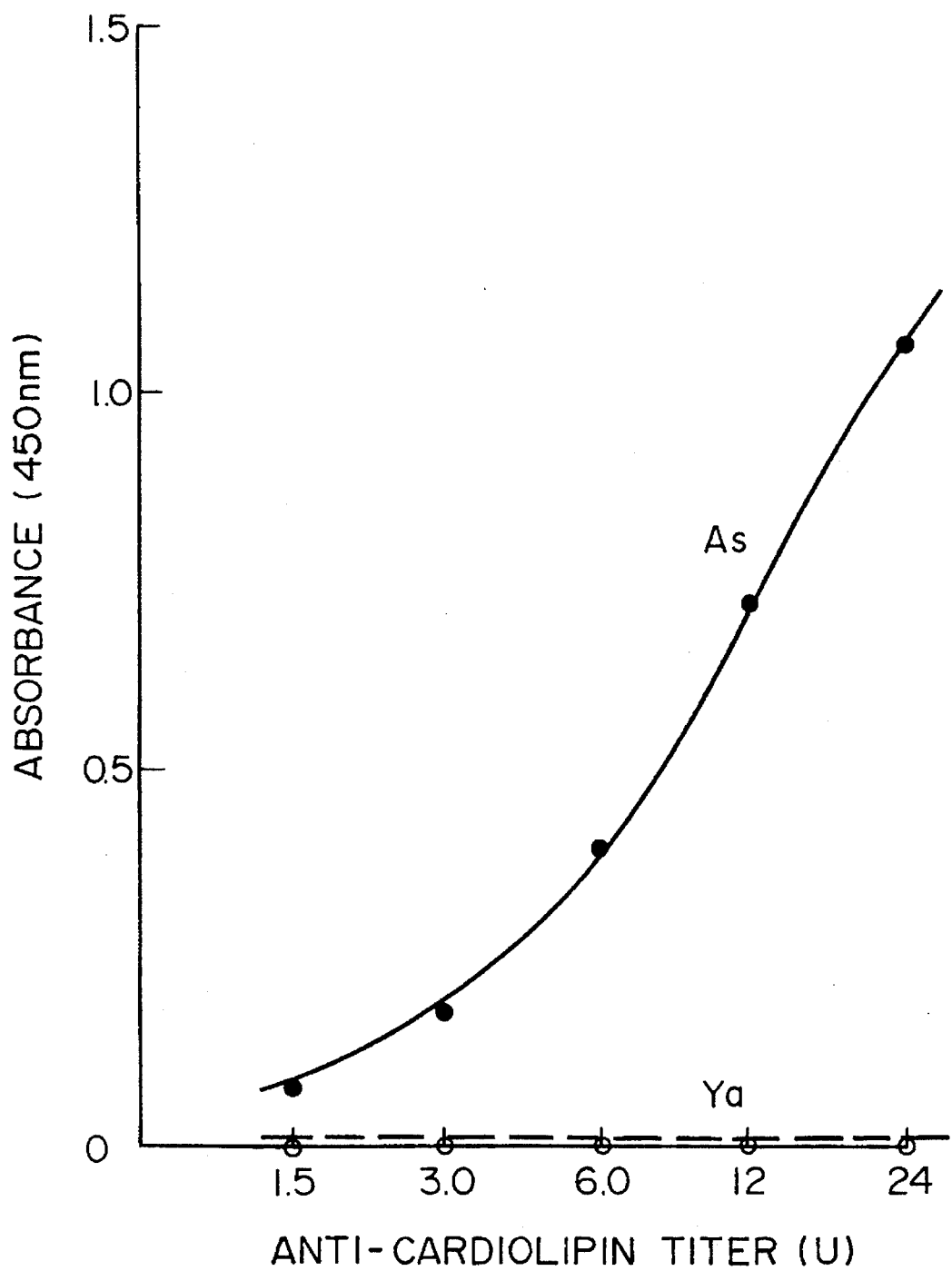

An ethanol solution of 50 μg/ml of bovine heart-derived cardiolipin (manufactured by Sigma Co., Ltd.) was charged in each well of a 96-well microtiter plate (polystyrene; manufactured by Titertech Co., Ltd.) in an amount of 50 μl/well. Ethanol in the well was dried up under reduced pressure. After drying up, phosphate buffered saline (PBS) (pH 7.4) containing 10% fetal bovine serum (hereafter abbreviated as PBS-FBS) was added to each well in an amount of 250 μl/well for blocking the well. After blocking at room temperature for an hour, all wells were washed 3 times with 250 μl of PBS containing 0.05% (V/V) Tween 20 (trademark, manufactured by Kishida Chemical Co., Ltd.) (hereafter abbreviated as PBS-Tween). Next, 100 μl each of sample solution (serum) appropriately diluted with PBS-FBS was charged in each well. The reaction was carried out at room temperature for an hour and then the well was washed 5 times with 250 μl of PBS-Tween. 100 μl each of horseradish peroxidase-labeled anti-human IgG antibody was added to each well. The reaction was carried out at room temperature for an hour and then the well was washed 5 times with PBS-Tween. After 100 μl of substrate solution (0.3 mM solution of 3,3', 5,5'-tetramethylbenzidine (TMBZ) containing 0.003% hydrogen peroxide) was added to the each well, the enzyme reaction was carried out at room temperature for 15 minutes. The reaction was terminated by adding 100 μl of stopping reagent (2N sulfuric acid solution) and then absorbance was measured at 450 nm. The results are shown in FIG. 1 (A). The enzyme-labeled antibody used was prepared by labeling mouse monoclonal anti-human IgG antibody (G-02, IgG class; manufactured by Yamasa Shoyu Co., Ltd.) with horseradish peroxidase according to the periodic acid crosslinking method. As the serum used herein as sample solution is serum (hereafter referred to as As serum) collected from the patient with typical antiphospholipid syndrome (recurrent abortion in SLE); Ya serum used herein as sample solution is serum (hereafter referred to as Ya serum) collected from the patient with tuberculous meningitis who has no symptom of antiphospholipid syndrome. As shown in FIG. 1 (A), it was impossible to differentially determine the antibody is As serum (hereafter referred to as As antibody) from the antibody in Ya serum (hereafter referred to as Ya antibody) according to the conventional method using fetal bovine serum (FBS) in the primary reaction.

Example 1

Detection of antibody specific to anti-phospholipid syndrome by adding sera from normal subjects (1) Preparation of a carrier for binding of anti-phospholipid antibody The carrier for binding of anti-phospholipid antibody was prepared by the following two methods.

[Method (I)]

An ethanol solution of 50 μg/ml of bovine heart-derived cardiolipin (manufactured by Sigma Co., Ltd.) was taken into each well of a 96-well microtiter plate (polystyrene; manufactured by Titertech Co., Ltd.) in an amount of 50 μl/well. Ethanol in the well was dried up under reduced pressure. After drying, PBS (pH 7.4) containing 1% (W/V) purified bovine serum albumin (manufactured by Sigma Co., Ltd.; No. 7511, fatty acid-free; hereafter abbreviated as pBSA) (hereafter abbreviated as PBS-pBSA) was added to the each well in an amount of 250 μl/well. After treating with PBS-pBSA at 4° C. for an hour, the well was washed 3 times with 250 μl of PBS containing 0.05% (V/V) Tween 20 (PBS-Tween) to give the carrier for binding of anti-phospholipid antibody of the present invention.

[Method (II)]

An ethanol solution of 500 μg/ml of bovine heart-derived cardiolipin (manufactured by Sigma Co., Ltd.) was taken into a glass-made test tube. After drying up under reduced pressure, PBS was added and cardiolipin was suspended to give a cardiolipin suspension. This cardiolipin suspension was taken into each well of a 96-well microtiter plate (polystyrene; manufactured by Titertech Co., Ltd.) in an amount of 50 μl/well. After reacting at 4° C. for an hour, the suspension was aspirated by suction. Thereafter the same procedure as in Method (I) was performed to give the carrier for binding of anti-phospholipid antibody of the present invention.

(2) Determination of anti-phospholipid antibody

Figure 2:
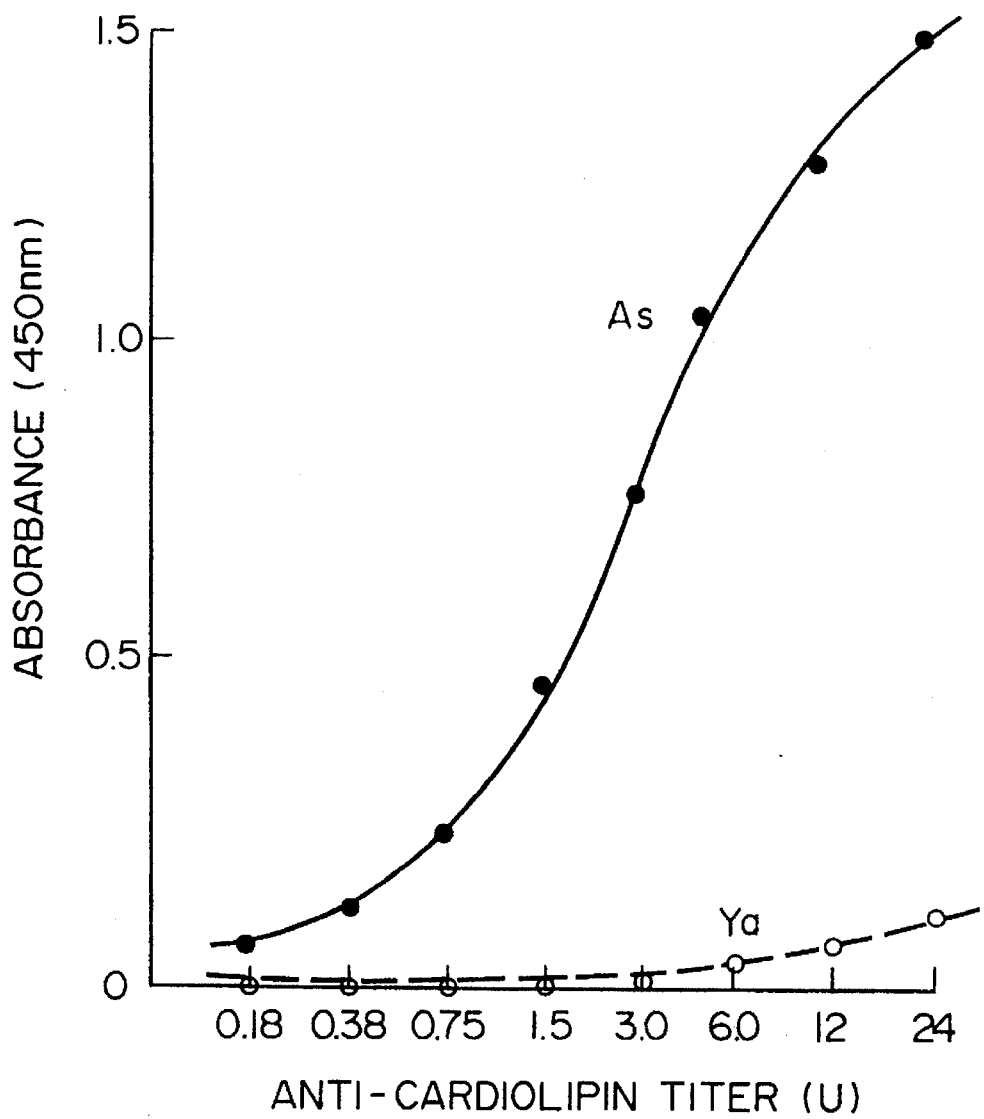
FIG. 2 indicates the absorbance (450 nm) measured as an index of antibody titer in As serum and in Ya serum, using a carrier for binding of the anti-phospholipid antibody prepared by procedures different from Example in FIG. 1 (C).

The same patient sera (i.e., As serum and Ya serum) as used in Reference Example were diluted with PBS-pBSA containing 5% human serum of normal subjects. Each diluted serum was taken into each well of the cardiolipin-bound titer plates previously prepared in Method (I) and Method (II) in an amount of 100 μl/well followed by reacting at 4° C. for an hour. The well was washed 5 times with 250 μl of PBS-Tween. Subsequent procedures were performed as in Reference Example and absorbance was measured (method of the present invention). The same procedure as described above was performed using the plate prepared by Method (I), except that the primary reaction was carried out by adding pBSA to the reaction solution, and the absorbance was determined (Comparative Example). The results obtained by the respective methods are shown by dilution curves. FIG. 1 (B) indicates the results of Comparative Example, FIG. 1 (C) shows the results obtained according to the method of the present invention using the plate prepared by Method (I), and FIG. 2 shows the results obtained according to the method of the present invention using the plate prepared by Method (II).

As is clear from FIG. 1 (B), binding ability of anticardiolipin antibody (Ya antibody) in Ya serum was reduced significantly (to about 20%) by replacing some of commercially available purified bovine serum albumin (pBSA) for fetal bovine serum (FBS) used in the primary reaction system in Reference Example. Also regarding As antibody, disappearance of the binding ability was noted with a specimen having a high dilution degree (namely, dilution of 200 times or more) in this case. By further adding serum (about 5%) from normal subjects to the basic assay system used in Comparative Example in which pBSA was added in the primary reaction, only As antibody titer was restored to almost the same as in the prior art method (Reference Example) using FBS. Turning to Ya antibody titer, it is disappeared completely.

Figure 3:
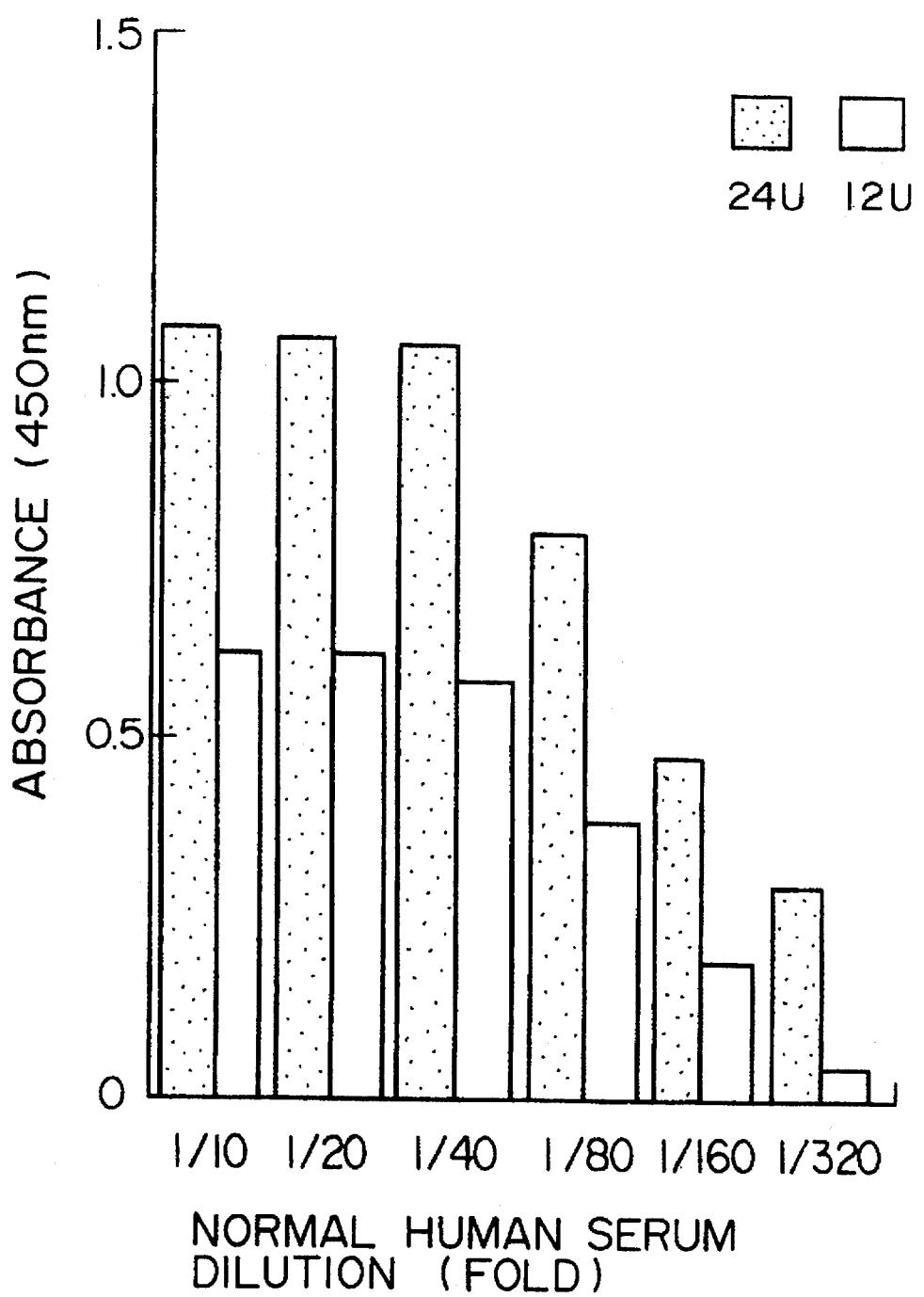
FIG. 3 shows relationship between concentration (dilution degree) of human sera from normal subjects supplemented and absorbance (450 nm) as an index of antibody titer.

By varying the concentration of sera from normal subjects added in the primary reaction, the reaction was carried out as described above to determine the antibody titer of As serum. Especially when the serum from normal subjects was added in a concentration as high as 1/40 of dilution or more, sufficient absorbance was obtained (FIG. 3). The samples assayed are As sera of 24 units (24 U) and 12 units (12 U) (according to the Harris et al.'s standarized unit).

Example 2

Figure 4:
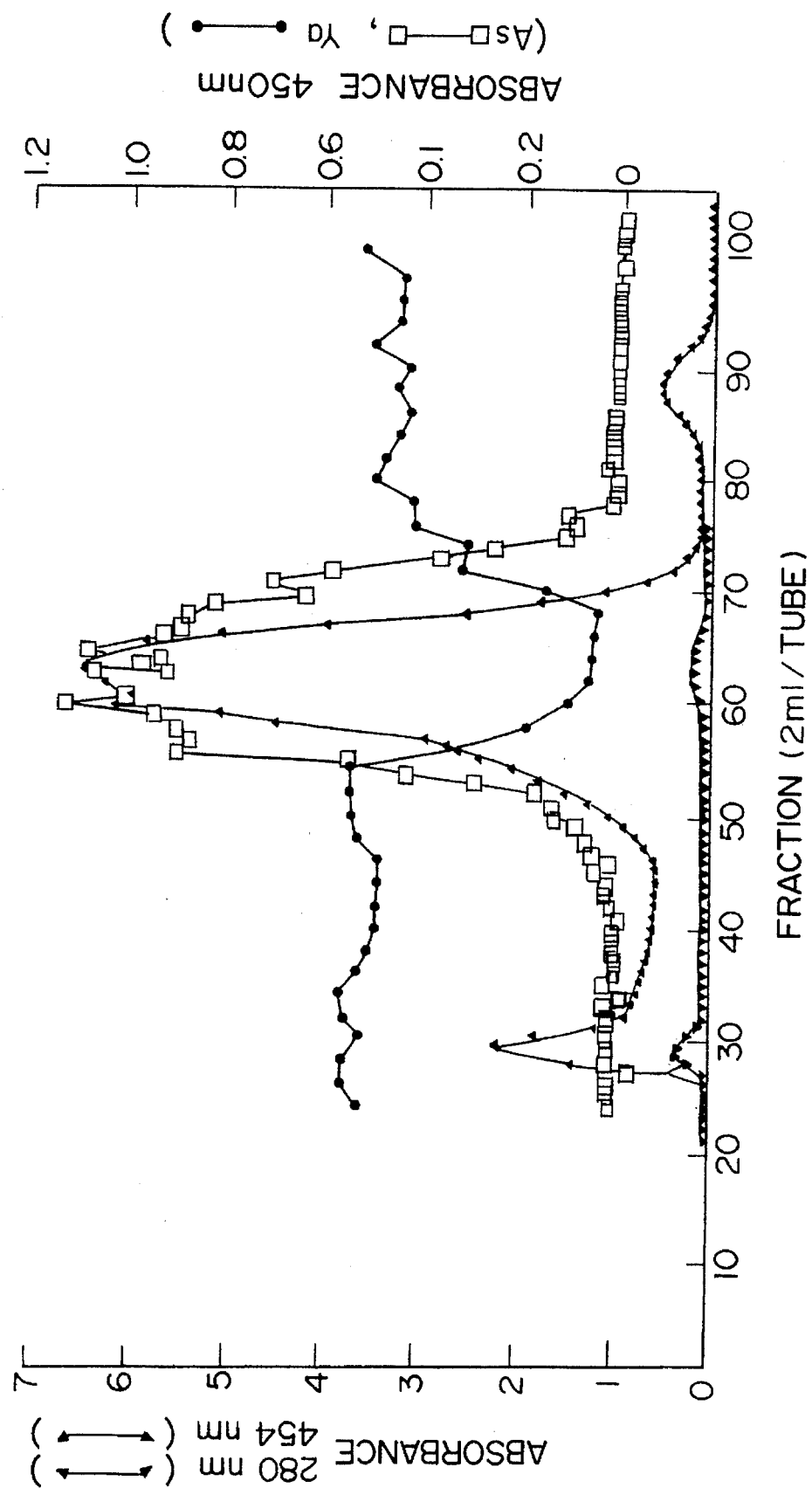
FIG. 4 shows relationship between gel filtration pattern of human sera from normal subjects and absorbance (450 nm) as an index of antibody titer in As serum and in Ya serum determined by performing the primary reaction under addition of each aliquot of the fraction.

Detection of antibody specific to antiphospholipid syndrome by adding the fraction of sera from normal subjects Sera from normal subjects was fractionated by gel filtration and each fraction was added to the reaction solution in the primary reaction. As the cardiolipin-bound plate, the plate prepared in Example 1, Method (I) was used. The procedures was performed as in Example 1 except that the sera from normal subjects were replaced with the fraction of the serum obtained by gel filtration. Then absorbance (450 nm) was measured as in index of the antibody titer. The fraction of serum from normal subjects was obtained by subjecting 3 ml of sera from normal subjects to gel filtration through Ultrogel ACA-34 (manufactured by LKB Co., Ltd.) column previously equilibrated and then fractionating by 2 ml each. FIG. 4 shows the relationship between pattern of gel filtration by Ultrogel ACA-34 and absorbance (450 nm) of As serum and Ya serum as an index of the antibody titer obtained by the procedures described above. The results indicate that the component (hereafter sometimes referred to as the active component) having the effects of enhancing the binding ability of As antibody to the carrier and striking out the binding ability of Ya antibody to the carrier was present in the second peak fraction out of the 3 absorption peaks at 280 nm in FIG. 4. The fraction also contained serum albumin. However, such activities (effects) were not recognized in purified human serum albumin itself and therefore, it was confirmed that the effects were not exhibited by serum albumin.

Furthermore, sera from normal subjects were fractionated by gel filtration according to HPLC using G2000SW (manufactured by Toso Co., Ltd.) column (0.75×30 cm). The fraction containing the active component (active peak) appeared around the serum albumin fraction and was eluted at the slightly lower molecular weight side (FIG. 5).

Figure 6:
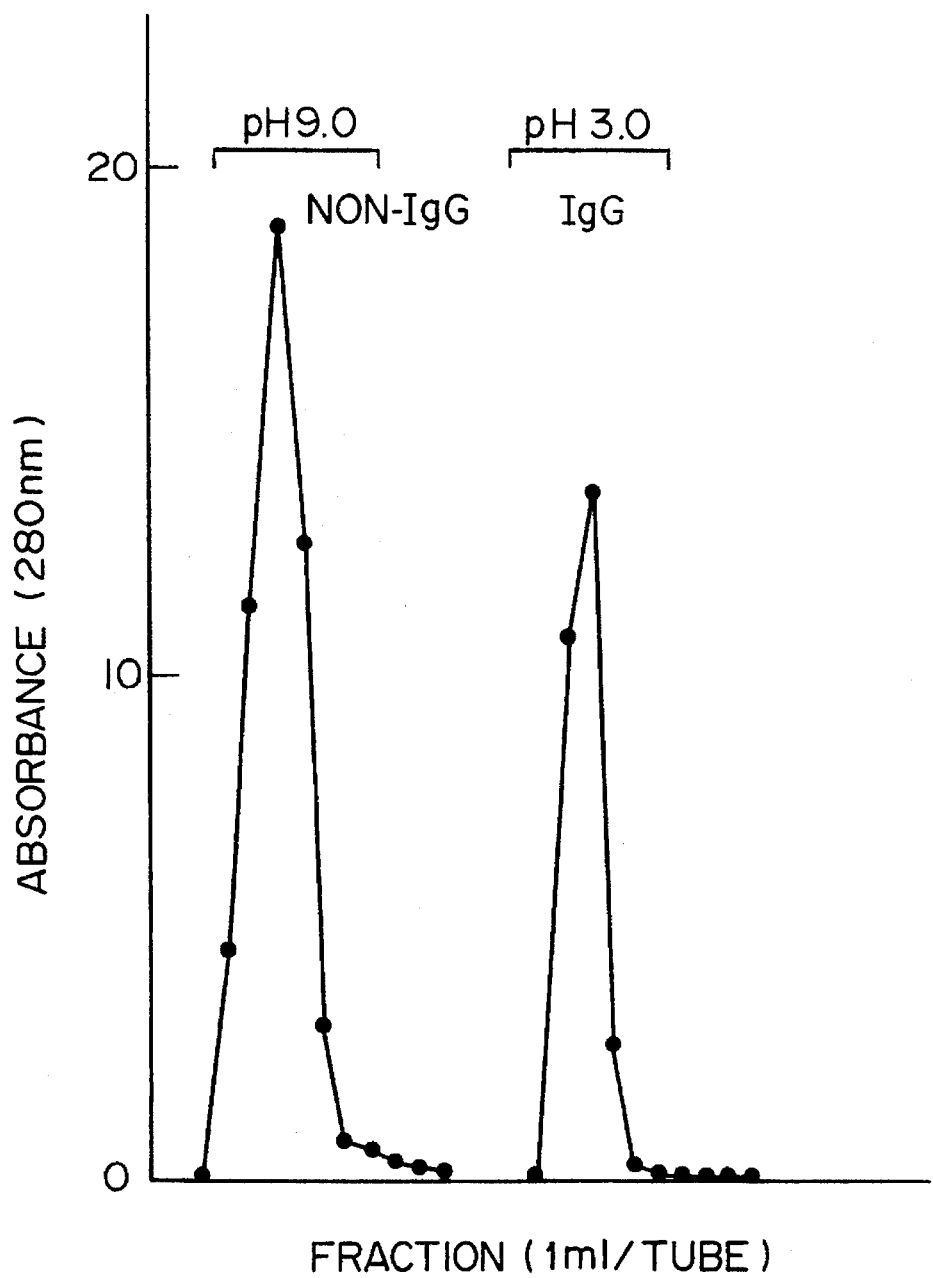
FIG. 6 shows a fractional pattern of sera from normal subjects by Protein A-Sepharose column.

Next, sera from normal subjects were dialyzed against 1M Tris-hydrochloride buffer (pH 9.0) and the dialysate was passed through a column packed with Protein A-Sepharose (manufactured by Pharmacia) to collect the effluent (non-IgG fraction) and the fraction (IgG fraction) was eluted with 0.1M citrate buffer (pH 3.0). FIG. 6 shows its elution pattern. Further after each probed fraction was dialyzed against PBS, an amount corresponding to the concentration of serum diluted to 1/20-fold was added to As serum (24 U). Using the plate prepared by Method (I), absorbance (450 nm) was determined as an index of the antibody titer in a manner similar to Example 1. The results are shown in Table 1.

TABLE 1

|  | Absorbence (450 nm) |
| --- | --- |
| Non-IgG fraction | 1.154 |
|  | (0.022) |
| IgG fraction | 0.806 |
|  | (0.676) |

In the table, values indicate absorbance at 450 nm and values with parentheses indicate the results measured in the absence of As serum sample (control experiment).

As shown in Table 1, the active component is present in the non-IgG fraction.

Figure 7:
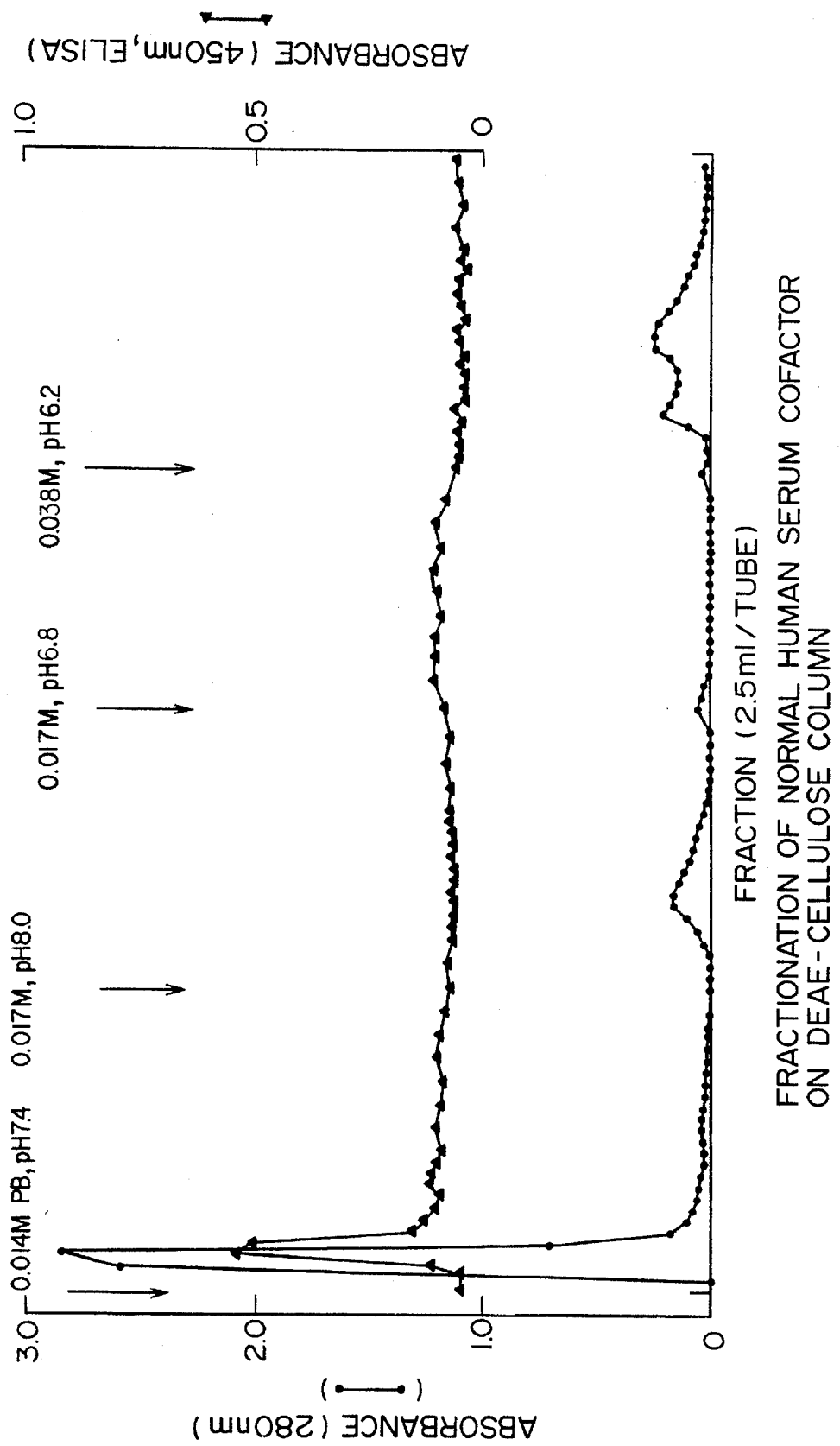
FIG. 7 shows elution profiles of human serum from normal subjects on DEAE-cellulose column chromatography, indicated by absorbance at 280 nm and at 450 nm (in ELISA) as an index of antibody titers in As serum.
Figure 8:
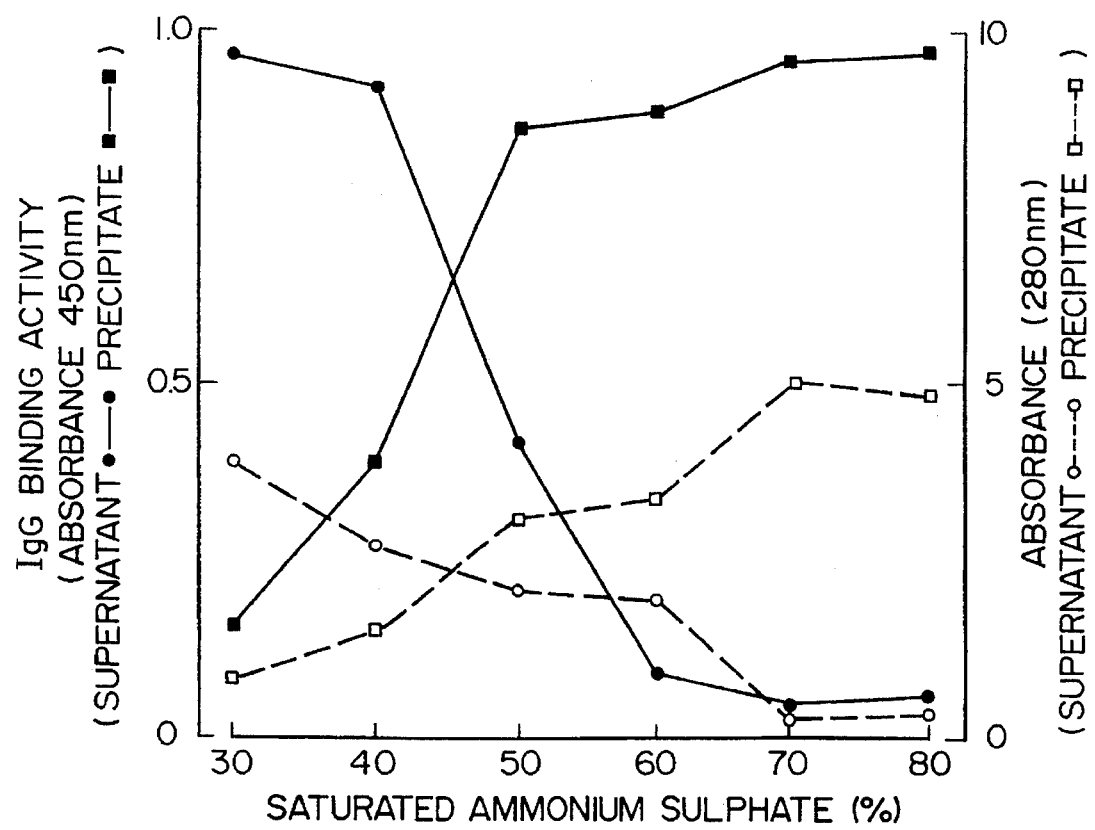
FIG. 8 shows relationship between fractionation of sera from normal subjects by ammonium sulfate and absorbance (450 nm) as an index of antibody titer in As serum.

In addition, sera from normal subjects were passed through DEAE-cellulose (manufactured by Whatmann Co., Ltd., DE-52) column. The active component appeared in the effluent and was eluted with 0.014M phosphate buffer (pH 7.4) (FIG. 7). When salting out was performed with ammonium sulfate, the active component precipitated in a concentration of 30 to 60% of saturation (FIG. 8).

It is considered that the effect of enhancing the binding ability of As antibody to the carrier would be achieved by the interaction of the above active component and the cardiolipin micelles on the solid phase and the effect of making the binding ability of Ya antibody to the carrier disappear would be achieved by the reaction of the active component and the Ya antibody in the liquid phase and by washing out of the complex thus formed.

Example 3

Detection of antibody specific to antiphospholipid syndrome by antigen-bound carrier treated with surfactant Using the carrier for binding of anti-phospholipid antibody treated only with Tween 20 obtained basically the same method as in Example 1, Method (I) and Method (II), except that the carrier was treated only with Tween 20, the effects of the method according to the present invention were examined.

That is, bovine heart-derived cardiolipin was bound to each well of a 96-well microtiter plate according to Method (I). The well was washed with PBS-Tween. In a manner similar to Example 1, human serum from normal subjects were added (Run I-1) or not added (Run I-2) to the reaction solution in the primary reaction to carry out the reaction and the following procedures were performed as in Example 1. As an index of the antibody titer, absorbance (450 nm) was measured. Furthermore, cardiolipin-bound well in a similar manner to the above was washed with PBS containing no Tween 20, and human serum from normal subjects were added (Comparison I-1) or not added (Comparison I-2) to the reaction solution in the primary reaction to carry out the reaction. The following procedures were performed as in Example 1. As an index of the antibody titer, absorbance (450 nm) was measured. For washing after the step of primary reaction and the step of secondary reaction, washing liquid corresponding to that described above was used, respectively, in each group.

Furthermore, bovine heart-derived cardiolipin was bound to each well of a 96-well microtiter plate in a manner similar to Method (II) described above, except that cardiolipin dried up in a test tube was suspended in PBS (pH 6.0) containing 0.01% BSA. The well was washed with 0.05% pPBS-Tween. In a manner similar to Example 1, human serum from normal subjects was added (Run II-1) or was not added (Run II-2) to the reaction solution in the primary reaction to carry out the reaction and the following procedures were performed as in Example 1. As an index of the antibody titer, absorbance (450 nm) was measured. In addition, cardiolipin-bound well by the same procedures was washed with PBS containing no Tween 20, and human serum from normal subjects was added (Comparison II-1) or not added (Comparison II-2) to the reaction solution in the primary reaction to carry out the reaction in a manner similar to Example 1. The following procedures were performed as in Example 1. As an index of the antibody titer, absorbance (450 nm) was measured. For washing after the step of primary reaction and the step of secondary reaction, PBS containing no Tween 20 was used as the washing liquid, respectively, in each group.

In the above runs, As serum and Ya serum were used as sample solutions. These sera are diluted to have a constant anti-phospholipid antibody titer, which was proposed by Harris, E. N. et al., in the Third International Symposium of Antiphospholipid Antibody at Kingston (KAPS).

The results of these runs are shown in Table 2.

In the table, the values indicate absorbance at 450 nm and the values with parentheses are values obtained by measurement using the cardiolipin-unbound carrier (control runs).

TABLE 2

| Group | As Serum (24 U) | Ya Serum (24 U) |
|---|---|---|
| Run I-1 | 0.982 | 0.032 |
|  | (0.011) | (0.012) |
| Run I-2 | 0.066 | 0.054 |
|  | (0.010) | (0.012) |
| Comparison I-1 | 1.280 | 1.109 |
|  | (1.124) | (1.082) |
| Comparison I-2 | 1.260 | 1.102 |
|  | (1.102) | (1.164) |
| Run II-1 | 0.998 | 0.053 |
|  | (0.022) | (0.050) |
| Run II-2 | 0.084 | 0.097 |
|  | (0.076) | (0.045) |
| Comparison II-1 | 1.125 | 1.100 |
|  | (1.025) | (1.028) |
| Comparison II-2 | 1.147 | 1.163 |
|  | (1.101) | (1.103) |

As shown in Table 2, antigenicity of cardiolipin is expressed by the washing treatment with Tween 20 so that the binding ability of As antibody of cardiolipin on the solid phase is enhanced and at the same time, non-specific adsorption of immunoglobulin to the plate is prevented. In the carrier for binding of anti-phospholipid antibody prepared by Method (I), it is considered that physically adsorbed cardiolipin on the carrier would cause lipid transfer onto micelles of Tween 20. The formation of "surfactant-phospholipid/-micelles" is essential for expressing the three-dimensional structure having antigenicity of cardiolipin on the surface of the plate. The micelles per se of Tween 20 also have the function of preventing the non-specific adsorption of immunoglobulin. Binding of the "surfactant-phospholipid/micelles" to the carrier can be effected not only by Method (I) but also by Method (II). Method (II) comprises firstly forming micelles of cardiolipin in a buffer solution, then incubating the micelles in a plate to adsorb cardiolipin onto the surface of the plate from lipid bilayer of the micelles and then washing with Tween 20.

Example 4

Effect of maintaining the expression of cardiolipin antigenicity by treatment with pBSA Using the cardiolipin-bound plate prepared in a manner similar to Method (I) described above, absorbance (450 nm) after the reaction similar to Example 1 was measured as an index of the titer of anti-cardiolipin antibody, by varying an concentration of Tween 20 used to treat the plate, in the case where the plate was treated with pBSA (1%, 4° C., 1 hour) (this invention) and in the case where the plate was not treated (comparative example). The results are shown in Table 3.

The treatment with the surfactant was made using PBS (pH 7.4) containing various concentrations of Tween 20. Samples assayed are As sera of 24 units (24 U) and 12 units (12 U) (according to Harris et al.'s unit).

TABLE 3

| Concentration | This Invention | | Comparative Example | |
|---|---|---|---|---|
| of Tween | 24 U | 12 U | 24 U | 12 U |
| 0 | 0.621 | 0.492 | 0.082 | 0.079 |
| 0.005 | 1.383 | 0.962 | 1.023 | 0.823 |
| 0.05 | 1.399 | 0.983 | 1.079 | 0.854 |
| 0.5 | 1.402 | 0.981 | 1.106 | 0.877 |

As is evident from Table 3, the expressing effect of antigenicity of Tween 20 was exhibited irrespective of treatment or non-treatment with pBSA. However, expression of the cardiolipin antigenicity was significantly accelerated by the treatment with 1% pBSA at 4° C. for an hour. That is, the formation of the physically three-dimensional conformation having antigenicity after the ethanol solution of cardiolipin was evaporated to dryness in Method (I) occurs not only by the treatment with Tween 20 but also by the treatment with pBSA. Further by the treatment using both Tween 20 and pBSA, expression of the antigenicity is accelerated and stability is also improved; there is also obtained the so-called "promoting effect of blocking" in which the non-specific adsorption of the antibody is prevented.

Example 5

Effect of various surfactants

By varying kind of surfactants used to treat the plate, absorbance (450 nm) was measured as an index of the antibody titer of As serum (24 U) in a manner similar to Example 4 according to the method of the present invention. The results are shown in Table 4. Each surfactant was used as 0.05% solution.

TABLE 4

| Surfactant | Absorbence (450 nm) |
|---|---|
| Tween 20 | 1.136 |
| Tween 60 | 1.025 |
| Tween 80 | 1.119 |

As is evident from Table 4, even though the surfactants having a different carbon chain length in the hydrophobic moiety from that of Tween 20, the effect similar to that with Tween 20 was obtained.

Example 6

Detection of antibody specific to anti-phospholipid syndrome by the carrier treated using human serum, pBSA and surfactant in combination The carrier for binding of anti-phospholipid antibody of the present invention was obtained in a manner similar to Example 1, Method (I) except that the cardiolipin-bound plate was treated with PBS containing 5% human serum from normal subjects and 1% (W/V) pBSA instead of the treatment with PBS containing 1% pBSA alone in Example 1, Method (I).

Using the above-mentioned carrier (this invention) and the carrier (comparison) obtained in Example 1, Method (I), absorbance (450 nm) was measured as an index of the antibody titer of As serum in a manner similar to Example 1 except for using 1% PBS-pBSA free of human serum from normal subjects in the reaction solution in the primary reaction. The results are shown in Table 5.

TABLE 5

| Group | 24 U | 12 U | 6 U |
| --- | --- | --- | --- |
| This Invention | 1.158 | 0.811 | 0.509 |
| Comparison | 0.169 | 0.095 | 0.035 |

As is obviously noted from Table 5, when the carrier for binding of anti-phospholipid antibody which was treated with human serum from normal subjects, pBSA and the surfactant in combination is used, the effect similar to the case where human serum was added was obtained even when no human serum was added in the primary reaction.

Example 7

Determination of sera from patients with antiphospholipid syndrome

Anti-cardiolipin antibody titers [unit (U)] in human serum samples collected from normal subjects and serum samples from patients with SLE (in the group of delivery and the group of miscarriage) were determined in a manner similar to Example 1, using the carrier for binding of anti-phospholipid antibody prepared in Example 1, Method (I). The results are shown in FIG. 9.

Figure 9:
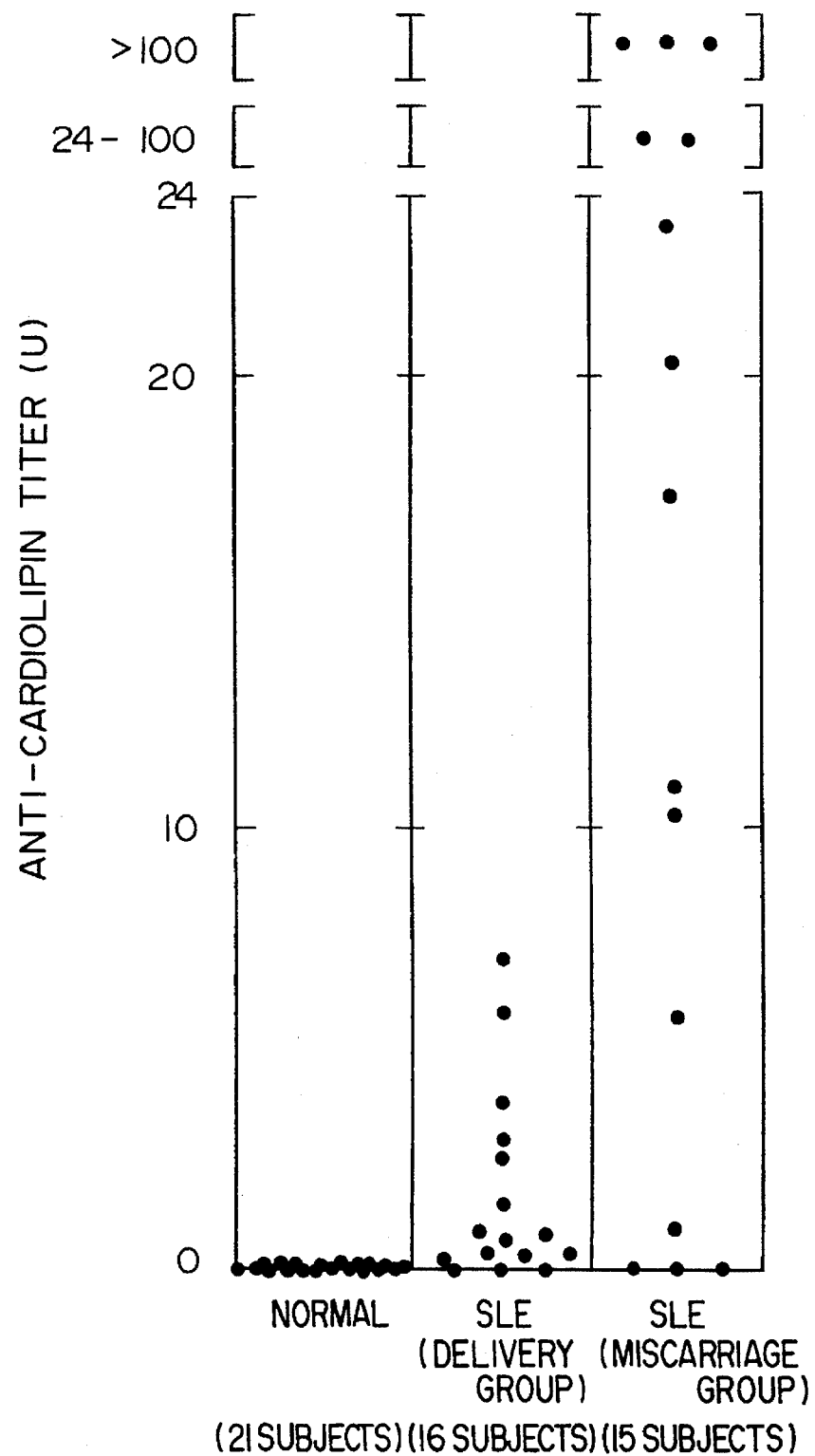
FIG. 9 indicates the results obtained by determining antibody titers (unit/ml; hereafter abbreviated as U) in sera from normal subjects and in sera from patients with antiphospholipid syndrome.

As shown in FIG. 9, the anti-cardiolipin antibody titer in the sera from the group of patients with SLE showed a significantly high level, as compared to that of the group of human serum from normal subjects. Further in the group of recurrent abortions, the antibody titer was significantly high as compared to the group of delivery (the group of successful delivery).

Figure 10:
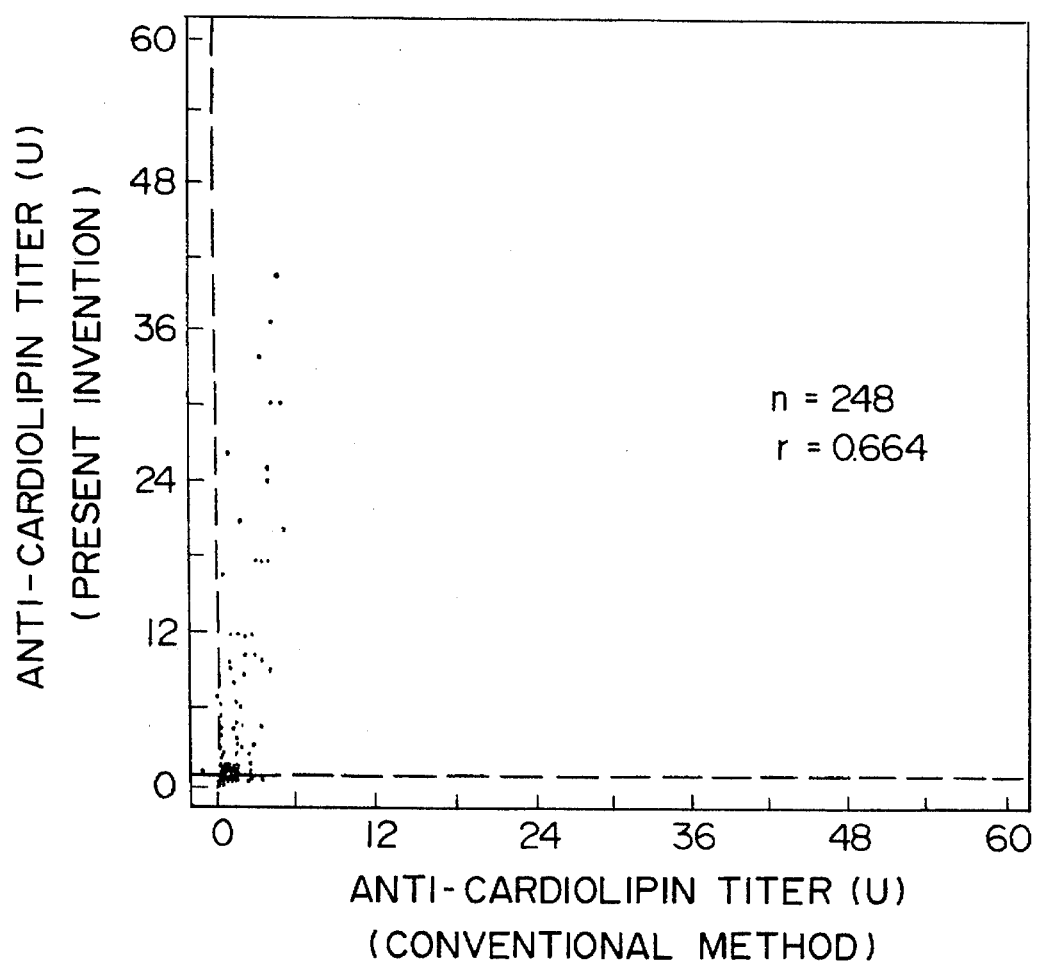
FIG. 10 indicates the correlation in antibody titers (U) of sera from patients with autoimmune disease(s) determined by the method of the present invention and a known method.
Figure 11:
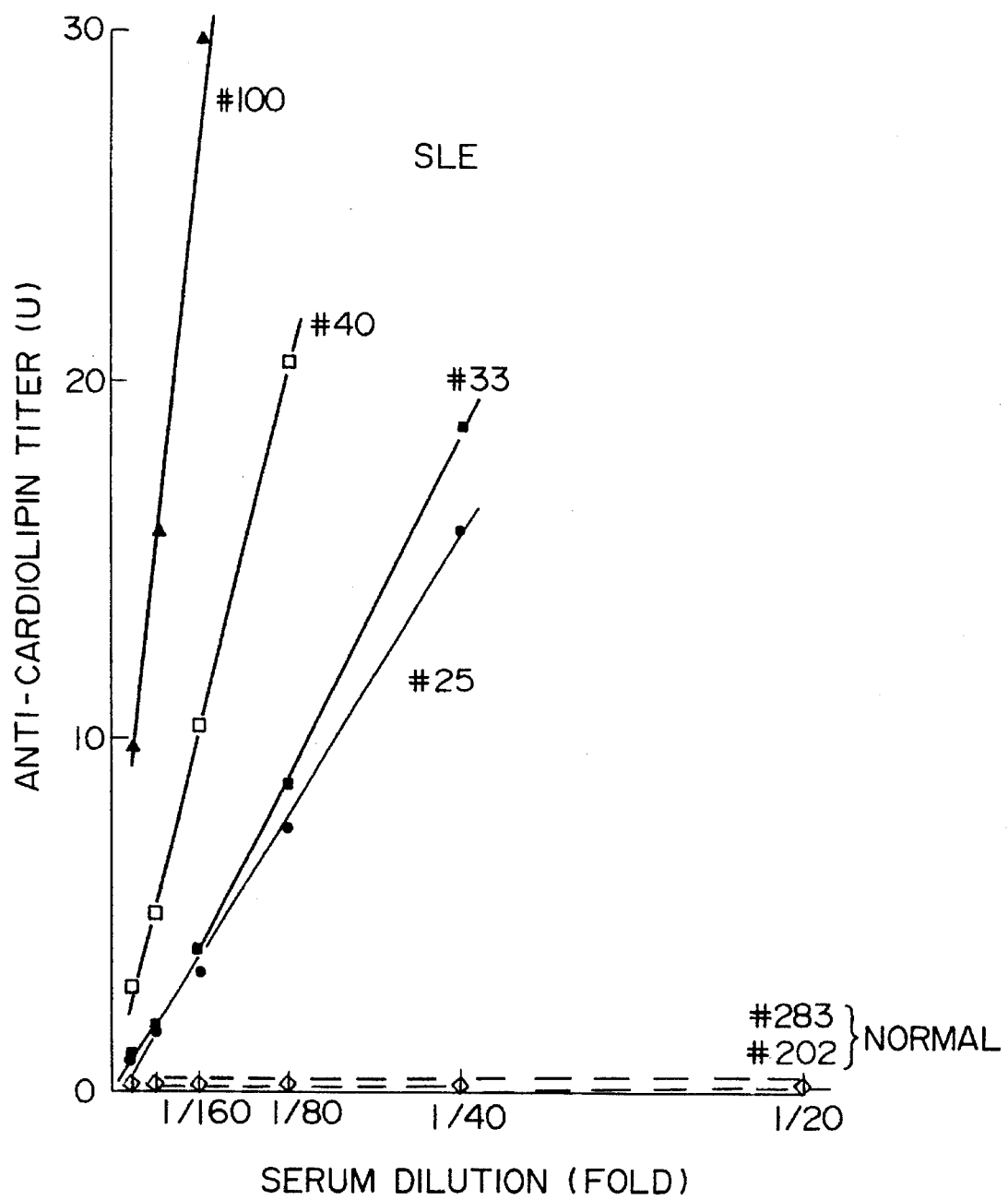
Figure 12:
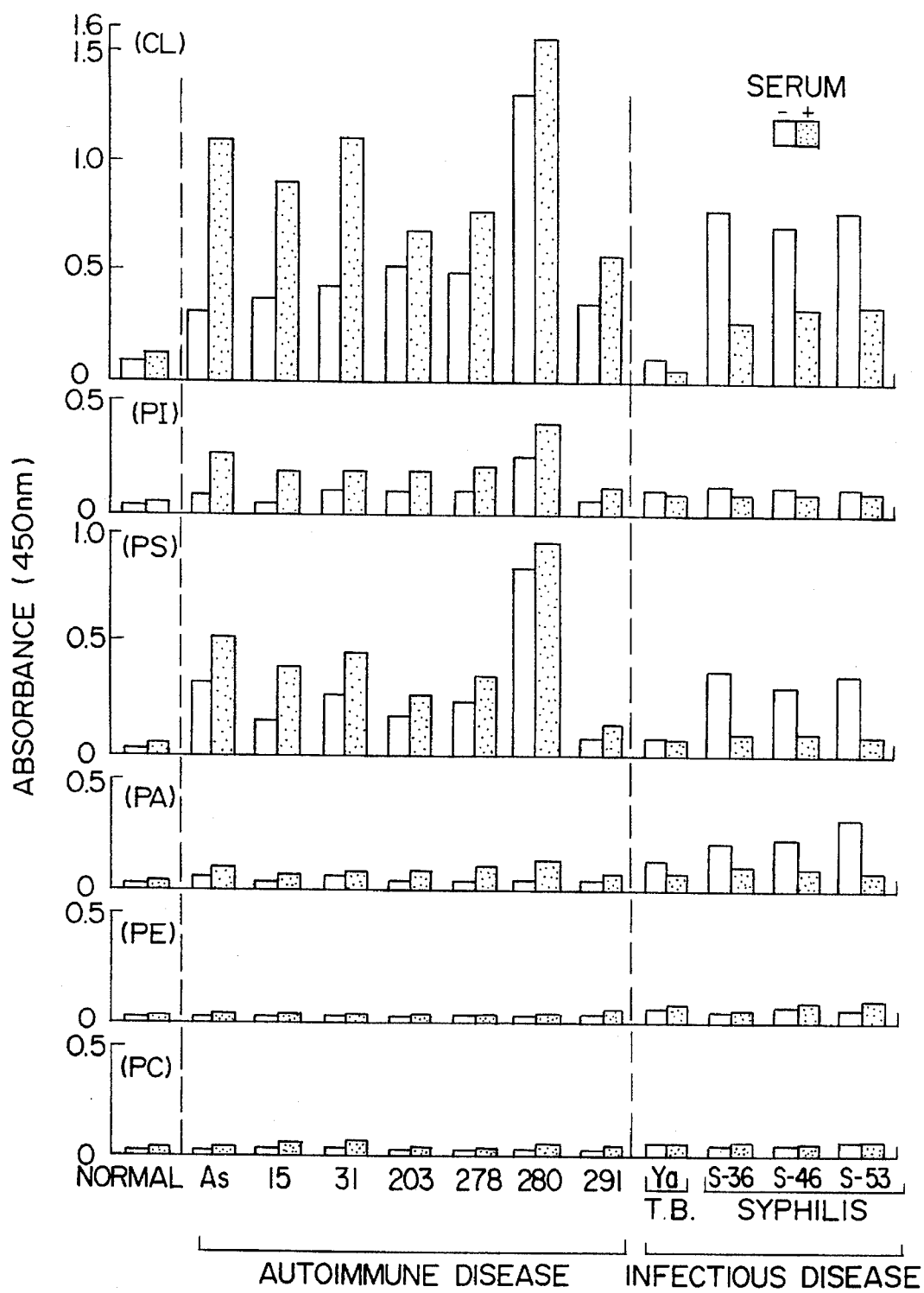

With respect to 248 sera collected from patients with autoimmune diseases including patients with SLE, the anti-cardiolipin antibody titer was also determined by conventional method (method shown in Reference Example) using fetal bovine serum in the primary reaction and by the method of the present invention described above, thereby to examine the correlation between these methods. The results are shown in FIG. 10. In FIG. 10, the ordinate indicates the antibody titer (unit) according to the method of the present invention and the abscissa indicates the antibody titer (unit) according to conventional method, and dotted line indicates cut-off value [average antibody titer in human sera from normal subjects +3X standard deviation (1 unit)]. Coefficient of correlation between the both assay systems is 0.664. According to the method of the present invention, independently quantitative determination is noted on a high level. That is, according to the method of the present invention, selection of positive and negative is more accurate. This is because the antibodies induced from infectious disease (namely, antibody of Ya type) is made negative as described above.

Figure 11:
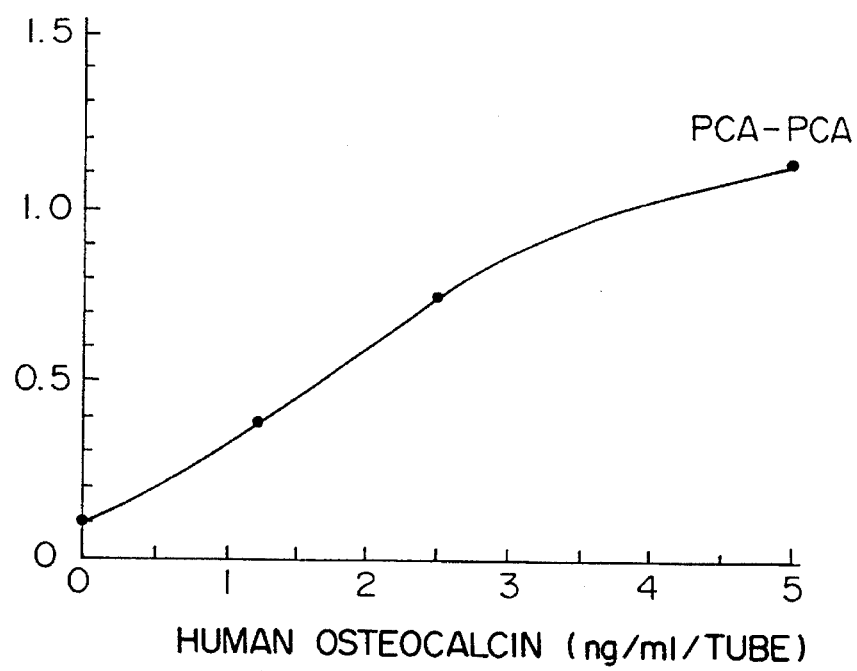
FIG. 11 indicates lineality in dilution of sera from patients with SLE according to the method of the present invention.

With respect to 4 human sera samples from the patients with SLE and 2 human sera samples from normal subjects, dilution curve [showing the relationship between dilution of sera and anti-cardiolipin antibody titer (unit)] was determined by the method of the present invention described above. The results are shown in FIG. 11. As is clear from FIG. 11, the method of the present invention provides extremely good linearity in dilution, indicating that accuracy of quantitative determination for the antibody titer is high.

Example 8

Comparison in anti-phospholipid antibody titer between sera from patients with autoimmune diseases and from patients with infectious diseases Using the carriers for binding of anti-phospholipid antibody prepared by binding various phospholipids in a manner similar to Example 1, Method (I), absorbance (450 nm) was measured in a manner similar to Example 1, as an index of the anti-phospholipid antibody titer in sera collected from patients with autoimmune diseases (SLE) and from patients with infectious diseases (tuberculous meningitis and syphilis).

Figure 12:
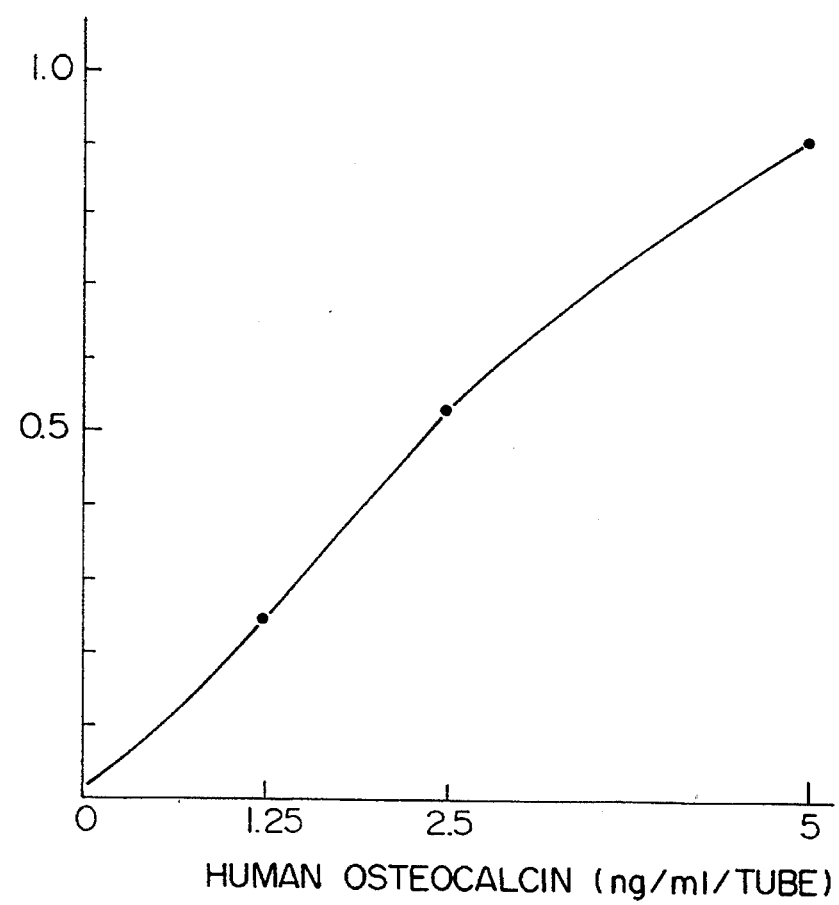
FIG. 12 indicates the results on sera of patients with autoimmune disease(s) and patients with infectious diseases (tuberculous meningitis, syphilis) obtained by determining absorbance (450 nm) as an index of antibody titer in the presence (halftone) and in the absence (white-on-black) of human serum according to the method of the present invention.

With regard to each of the serum samples, the antibody titer was examined in the presence or absence of 5% human serum from normal subjects. The results are shown in FIG. 12. As serum was 24 U (diluted to a concentration of 1/200-fold) and the other sera were all diluted to 1/100-fold concentration and provided for test. In the figure, each reactivity of the anti-phospholipid antibody in each serum sample is shown, in the order going down from the upper part, when using cardiolipin (CL), phosphatidylinositol (PI), phosphatidylserine (PS), phosphatidic acid (PA), phosphatidylethanolamine (PE) and phosphatidylcholine (PC), respectively, as the solid phase bound antigen (wherein CL, PI, PS and PA fall within the present invention and PE and PC indicate comparative examples). In this case, the amount of the antigen used is 2.5 µg/50 µl/well.

As is clearly noted from FIG. 12, the autoimmune disease-induced antibodies (antibodies specific to autoimmune diseases) showed the reactivity potentiated dependently on the addition of the human serum, whereas in the infectious disease-induced antibodies (antibodies induced from infectious diseases), the reactivity decreased dependently on the addition of the human serum. The results indicate that the infectious disease- and autoimmune disease-induced anti-phospholipid antibodies, which were differentially determined only with difficulty by the conventional method, could be independently determined.

Example 9

Effect of buffer

Using the carrier for binding of anti-phospholipid antibody prepared according to Example 1, Method (I), absorbance (450 nm) was measured, as an index of the antibody titer of As serum, in a manner similar to Example 1 except for using HEPES buffer (10 mM HEPES, 150 mM NaCl, pH 7.4) containing 1% pBSA as diluent of the sample solution. The results are shown in FIG. 13.

Figure 13:
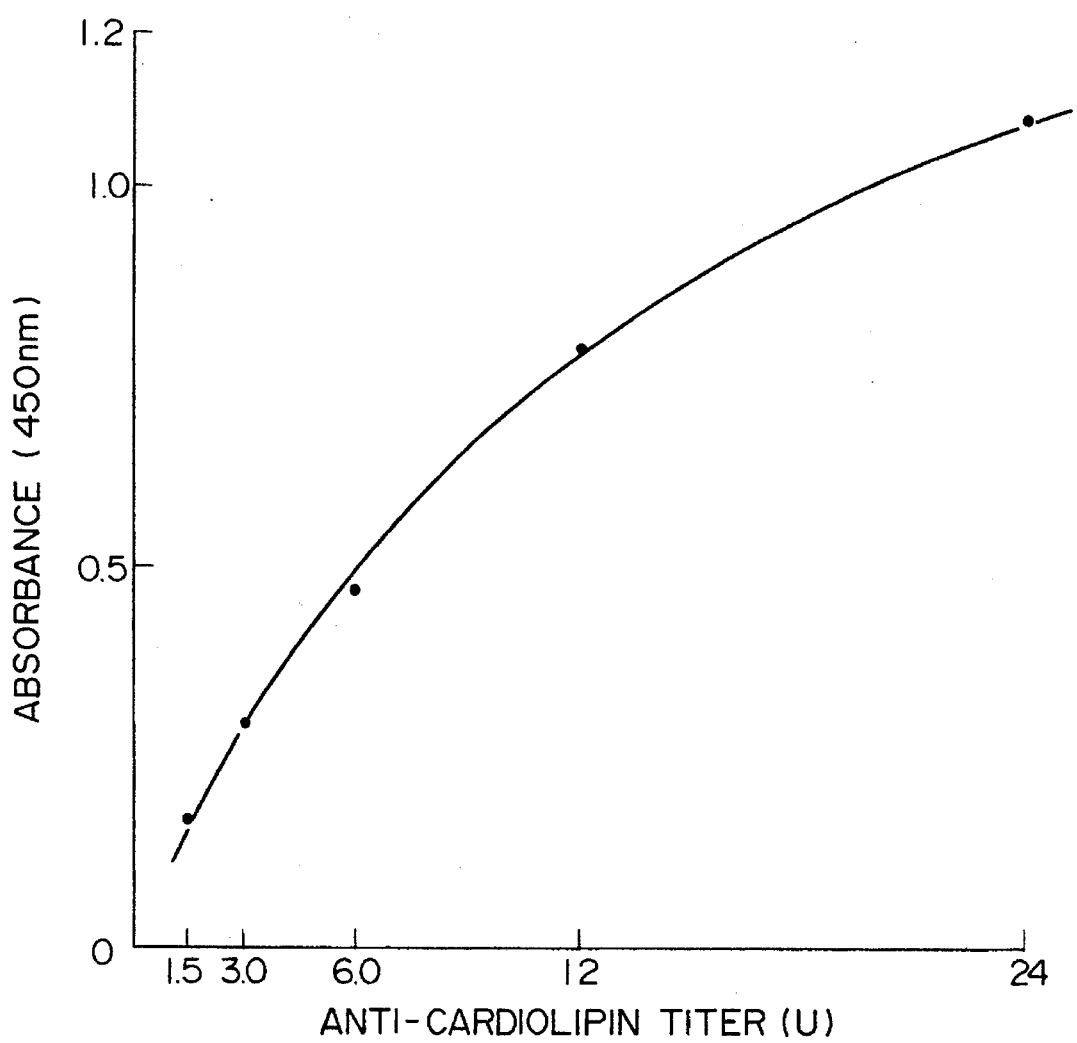
FIG. 13 shows absorbance (450 nm) on the reaction with As serum using buffer containing HEPES as the primary reaction solution, based on which a calibration curve of antibody titers was prepared.

As is evident from FIG. 13, a good calibration curve [showing the relationship between anti-cardiolipin antibody titer (unit) and absorbance (450 nm)] was obtained when the reaction solution containing HEPES was used as the reaction solution (diluent of the sample solution) in the primary reaction, indicating that the use of the buffer is useful for determination of the anti-phospholipid antibodies induced from antiphospholipid syndrome.

Example 10

Purification of the active component

The active component in the fraction of human serum from normal subjects mentioned in Example 2 (hereafter referred to as anticardiolipin cofactor) was purified as follows.

Figure 14:
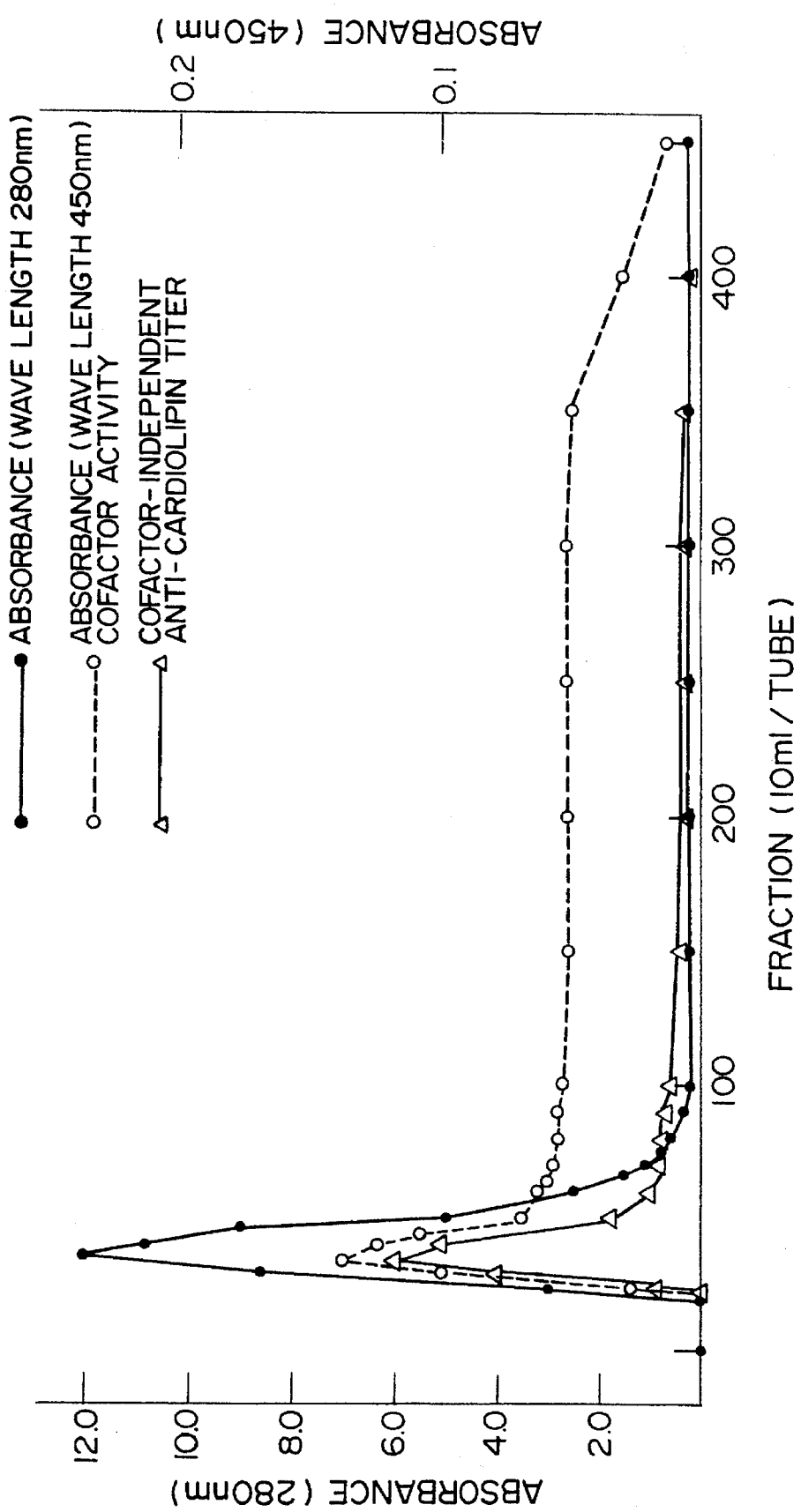
FIG. 14 shows a chromatogram of sera from normal subjects by ion exchange chromatography on DEAE-cellulose (DE-52) column.

(A) Purification procedure (1) Ion exchange column chromatography of human serum from normal subjects by DEAE-cellulose (E-52) column In order to purify the active component from human serum from normal subjects, ion exchange column chromatography was performed using DEAE-cellulose (DE-52; manufactured by Whatmann Co.). That is, 150 ml of DE-52 ion exchange resin, which had been previously activated in a conventional manner, was packed in a glass-made column of 2.5×60 cm and then equilibrated with 14 mM sodium phosphate buffer (pH 7.4). After 100 ml of human sera dialyzed against 3 liters of the same buffer for 2 days were added from the top of the column, the elution was carried out with 3 liters of the same phosphate buffer. The eluate was fractionated by 10 ml each with a fraction collector. By measuring the absorbance of each fraction at a wavelength of 280 nm, the elution profile of protein was monitored. Furthermore, the activity of anti-cardiolipin cofactor was determined by Method (B) described hereinafter. In addition, the activity of anti-cardiolipin antibody independent of the cofactor was also determined by Method (B), since the activity appeared in the case where human serum from normal subjects was subjected to ion exchange column chromatography by DEAE-cellulose. From them, the fraction showing the cofactor activity was recovered (FIG. 14). The recovered active fractions were concentrated to about 100 ml by ultrafiltration or salting out with 80% saturated ammonium sulfate, in a conventional manner. The concentrate was subjected to Protein A-Sepharose column chromatography.

Figure 15:
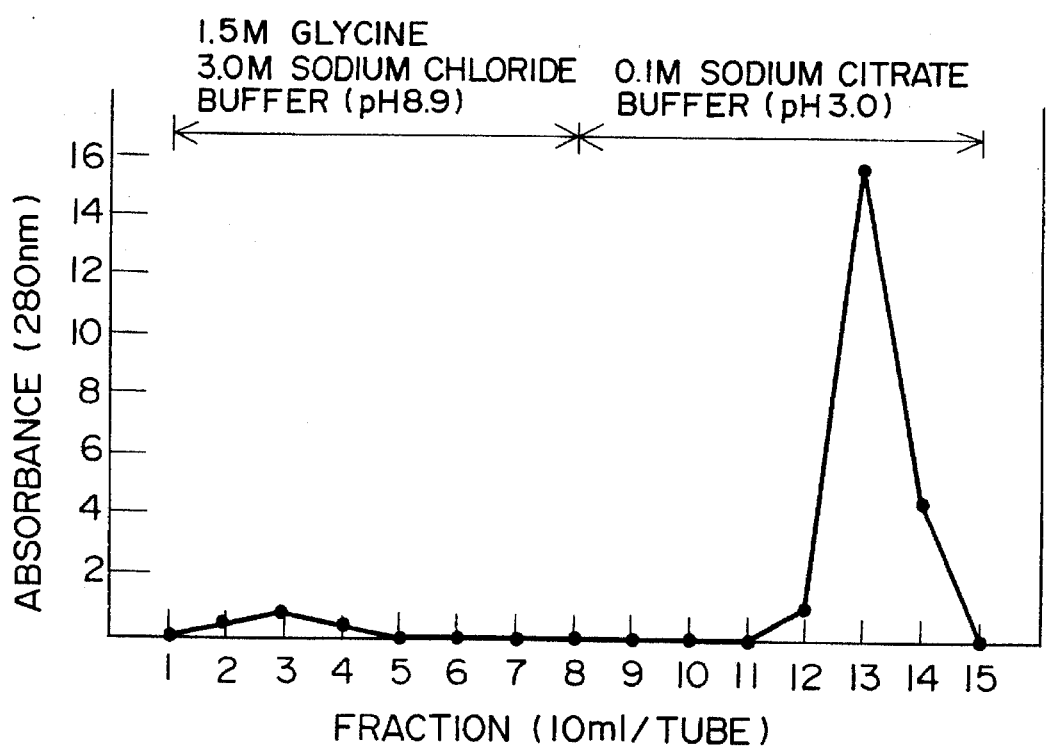
FIG. 15 shows a chromatogram obtained by subjecting the fraction containing anticardiolipin cofactor activity obtained by the ion exchange chromatography shown in FIG. 14 to Protein A-Sepharose column chromatography.

(2) Protein A-Sepharose column chromatography of the fraction containing the cofactor activity In order to remove human IgG from the fraction containing the cofactor activity, Protein A-Sepharose column chromatography was performed. That is, 20 ml of Protein A-Sepharose (manufactured by Pharmacia) was packed in a glass-made column of 1.5×20 cm and equilibrated with 1.5M glycine buffer (pH 8.9) containing 3M sodium chloride. After 10 ml of the previously obtained active fraction was diluted with the same volume of the glycine buffer, the resulting diluted solution was added from the top of the column. Elution was performed with 100 ml of the same glycine buffer. The eluate was fractionated by 10 ml each with a fraction collector. With regard to each fraction thus obtained, the absorption of protein was measured in a manner similar to the above and the peak fraction of the absorbance was recovered (FIG. 15). After the recovered fraction was dialyzed overnight against 2 liters of 10 mM HEPES buffer (pH 7.4) containing 150 mM sodium chloride, the dialysate was concentrated to 5 ml with a ultrafiltration device. The concentrate was then subjected to affinity column chromatography shown below. The adsorbed IgG was eluted with 100 mM sodium citrate buffer (pH 3.0).

Figure 16:
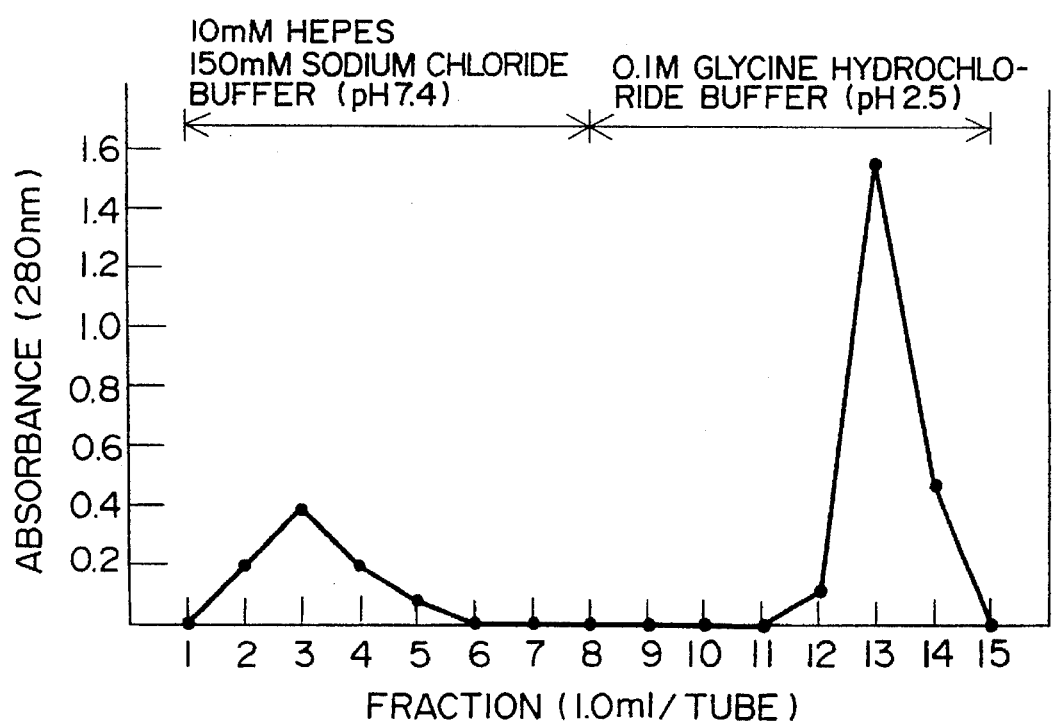
FIG. 16 shows a chromatogram obtained by subjecting the fraction containing anticardiolipin cofactor activity obtained by the chromatography shown in FIG. 15 to affinity column chromatography through anti-human IgG antibody conjugated Sepharose CL-4B column.

(3) Affinity chromatography by anti-human IgG antibody conjugated Sepharose CL-4B column In order to remove non-adsorbed IgG to protein A, Affinity column chromatography was performed using a resin prepared by binding anti-human IgG antibody to Sepharose CL-4B resin (manufactured by Pharmacia). That is, the previously prepared resin was packed in a glass-made column of 2.0×5 cm, which had been equilibrated with 10 mM HEPES-sodium buffer (pH 7.4) containing 150 mM sodium chloride. After 1 ml of the solution obtained in (2) was added from the top of the column. Concentrate was then washed with the same HEPES buffer. The effluent was fractionated by 1 ml each with a fraction collector. With regard to each fraction thus obtained, the absorption of protein was measured in a manner similar to the above and the fractions of the absorbance peak fractions were recovered (FIG. 16). The recovered fractions were collected into one and subjected to sodium dodecyl sulfate (hereafter abbreviated as SDS) polyacrylamide gel electrophoresis. After it was confirmed that IgG was completely removed (FIG. 17, Fr. 1N) by the electrophoresis, the collected fraction was concentrated to 2 ml with a ultrafiltration device. The adsorbed IgG was eluted with 0.1M glycine hydrochloride buffer (pH 2.5).

(4) Purification of the cofactor by cardiolipin-liposomes,

By affinity adsorption to cardiolipin-liposomes, the cofactor was completely purified from the purified fraction (hereafter referred to as Fr.1N) obtained in (3), from which IgG had been completely removed. That is, 2 ml of ethanol solution of 5 mg/ml of cardiolipin was charged in a pear type flask of 25 ml volume and the solution was mildly evaporated to dryness under reduced pressure so as to form a thin film on the wall surface of the flask. After 2 ml of 10 mM HEPES buffer (pH 7.4) containing 150 mM sodium chloride was added thereto, the mixture was vigorously stirred for 15 minutes with a vortex mixer to prepare cardiolipin-liposomes. The thus prepared liposomes were added to the solution of purified fraction, Fr.1N (1.2 mg/ml, in the same HEPES buffer) obtained in (3) in the same volume. The mixture was settled at room temperature for an hour to adsorb the cofactor to the liposomes by affinity. Next, the liposomes were recovered by centrifugation at 4° C. at 15,000 rpm for 15 minutes. The liposomes were washed by centrifugation 3 times with the same HEPES buffer. Each supernatant was recovered. It was confirmed that the supernatant was free of the cofactor not adsorbed to the liposomes by SDS polyacrylamide slab gel electrophoresis in a conventional manner. Where the cofactor not adsorbed to the liposomes was present in the supernatant, similar procedures were repeated and the cofactor was adsorbed to the liposomes to recover. The liposomes to which the cofactor was thus adsorbed were suspended in 100 to 500 µl of the same HEPES buffer and the suspension was stored by freezing at −20° C. Using the cofactor-adsorbed liposomes obtained by the procedures, SDS polyacrylamide slab gel electrophoresis was performed in a conventional manner. Thus, there were obtained protein(s) appearing as double patterns at about 50,000 of molecular weight which were very close to each other (FIG. 17, F-1). At the same time, the cofactor was purified in a similar manner, using 2 mM liposome of dipalmitoyl phosphatidylcholine (DPPC): cardiolipin (80:20, mol %) and 2 mM liposomes of DPPC: dipalmitoyl phosphatidylethanolamine (DPPE) (80:20, mol %). As the result, the liposomes composed of DPPC and cardiolipin showed the effect similar to that achieved by the liposome composed of cardiolipin alone (FIG. 17, F-2). However, the component supposed to be the cofactor was not adsorbed to the liposome composed of DPPC and DPPE (FIG. 17, F-3).

(5) Isolation of the cofactor adsorbed to liposomes by HPLC

Figure 18:
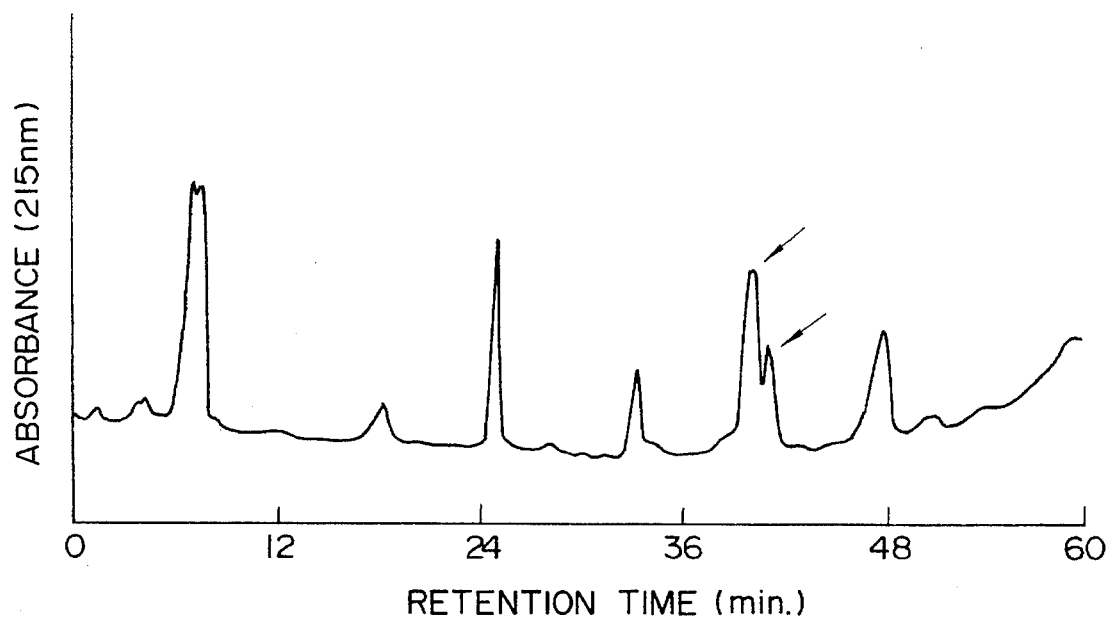
FIG. 18 shows a chromatogram of HPLC obtained by subjecting the anticardiolipin cofactor purified with liposome.

The cofactor purified by affinity adsorption to cardiolipin-liposome was isolated by HPLC using reverse phase chromatography column. That is, a suspension of the cofactor-adsorbed liposome was centrifuged at 15,000 rpm for 15 minutes to recover liposome. Then 1% SDS aqueous solution was added thereto and the mixture was thoroughly stirred to sufficiently dissolve liposome. The solution was again centrifuged under the same conditions to precipitate the insoluble matter. The supernatant was subjected to HPLC under the following conditions using reverse phase chromatography column [Waters Microbonders Pair C-4 column (3.9×15 cm); manufactured by Waters], while monitoring the absorbance at 215 nm with an absorbance detector appended. The purified cofactor was thus obtained (FIG. 18).

| Conditions for HPLC for isolating the cofactor from the cofactor-adsorbed cardiolipin-liposome | |
|---|---|
| Flow rate | 1 ml/min. |
| Upper limit of pressure | 300 kgf/cm$^2$ |
| Lower limit of pressure | 0 kgf/cm$^2$ |
| Flow time | 60 minutes |
| Feeding solutions used: | |
| Solution A: | 0.1% trifluoroacetic acid aqueous solution |
| Solution B: | mixture of acetonitrile isopropanol (3:7, v/v) added with 0.07% trifluoroacetic acid |

| Conditions for gradient of feeding solutions: | | |
|---|---|---|
| Time | Solution A (%) | Solution B (%) |
| 0 min. after | 100 | 0 |
| 60 mins. after | 40 | 60 |

(6) Molecular weight and isoelectric point of anti-cardiolipin cofactor

Figure 19:
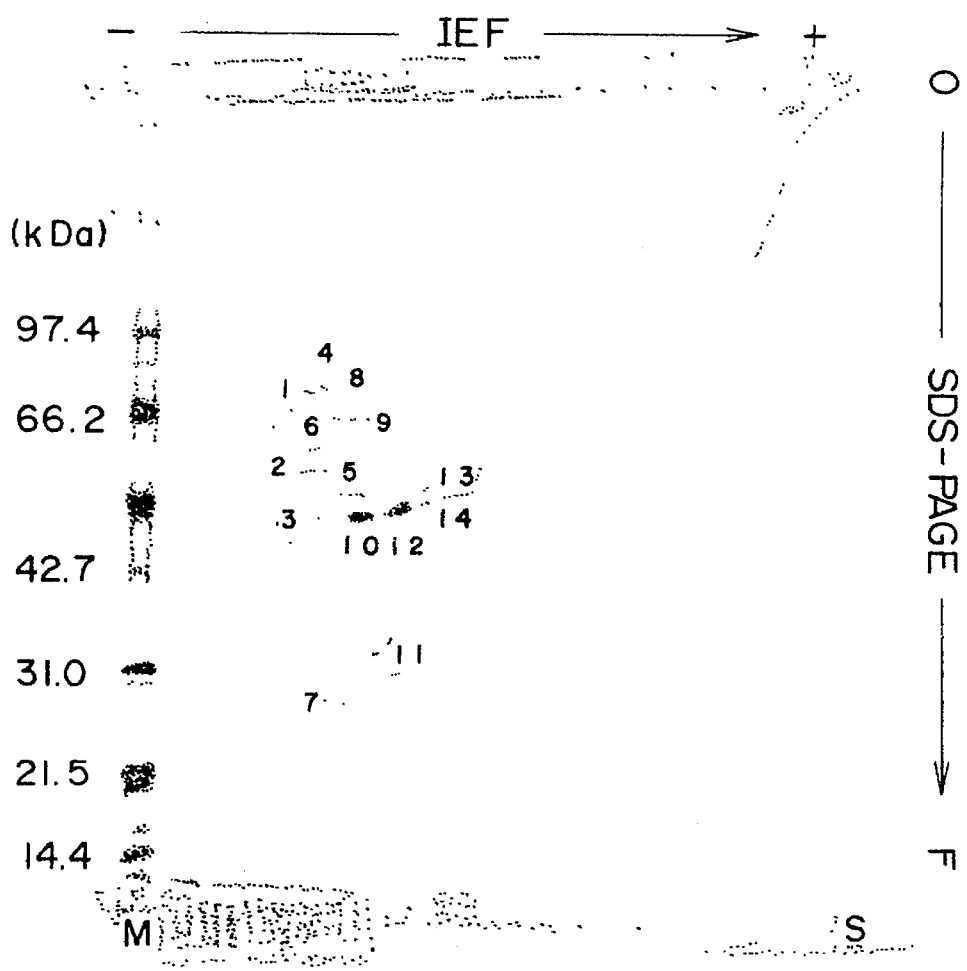
FIG. 19 shows the results obtained by subjecting to ISODALT electrophoresis the fraction containing anticardiolipin cofactor activity obtained by the affinity column chromatography through anti-human IgG antibody conjugated Sepharose CL-4B column shown in FIG. 16.

In order to examine the isoelectric point and molecular weight of the cofactor, ISODALT gel electrophoresis was performed according to the method of Anderson et al. Firstly, the solution Fr.1N obtained in (3) was subjected to the electrophoresis (FIG. 19). As shown in FIG. 19, several spots appeared. The results of SDS polyacrylamide gel electrophoresis (FIG. 17, F-1) on the purified cofactor obtained in (5) reveal that the cofactor adsorbed to cardiolipin-liposome correspond to Spot Nos. 10 and 12 shown in FIG. 19. That is, the isoelectric point and molecular weight of the cofactor were identified from FIG. 19 to be 6.75 and 49,000 (No. 10) and 6.60 and 50,000 (No. 12), respectively. These two components correspond to proteins having the same amino acid sequence but having different sugar chains or having some of amino acids somehow modified on the functional groups thereof, which are considered to be the subtype of the cofactor.

(B) Method for determining the anticardiolipin cofactor activity and the cofactor-independent anti-cardiolipin antibody activity The anticardiolipin cofactor activity and the cofactor-independent anti-cardiolipin antibody activity contained in human sera from normal subjects were determined by the following method.

These activities were determined in a manner almost similar to the method shown in Reference Example.

That is, a 96 well microplate coated with cardiolipin was washed with 200 μl/well of PBS buffer (pH 7.4) containing 0.05% Tween 20 (hereafter referred to as washing liquid). This procedure was repeated 3 times to activate the plate. A sample to be assayed was pipetted by 50 μl each per well. Next, 50 μl of As serum which had been previously diluted to 200-fold with 10 mM HEPES buffer (pH 7.4) containing 150 mM sodium chloride and 1% pBSA (hereafter referred to as diluting buffer), was pipetted in the well in which the cofactor activity was to be determined. On the other hand, 50 μl each of the diluting buffer was pipetted in the well in which the cofactor-independent anti-cardiolipin antibody activity was to be determined. The plate was allowed to stand at room temperature for 30 minutes. The following procedures were the same in the two systems. That is, both wells were washed 3 times with the washing liquid and 100 μl each of the solution of anti-human IgG antibody labeled with horseradish-derived peroxidase, which was diluted with 10 mM HEPES buffer (pH 7.4) containing 150 mM sodium chloride, 1% pBSA and 1 mM EDTA, was pipetted in the wells, respectively. The plate was allowed to stand at room temperature for 30 minutes. After washing with the washing liquid further 3 times, aqueous solution (100 μl) containing 0.3 mM TMBZ and 0.003% hydrogen peroxide were added to the plate as substrate solution. After reacting for 10 minutes, absorbance was measured at 450 nm with a plate reader.

Test Example

In order to examine the properties of the anticardiolipin cofactor, the following experiment was performed.

(1) Preparation of biotinylated anticardiolipin cofactor

According to a modified method of Kumagai and Okumura et al. described in MENEKI-JIKKEN SOSAHO (Procedures for Immunological Experiment) [published Feb. 20, 1980 by Association of Immunology, Japan (Chapter III. Cellular Antigen 15–59, page 2425)], 1 mg of the anticardiolipin cofactor purified in Example 10(3) was biotinylated to label the anticardiolipin cofactor.

(2) Binding ability of the anticardiolipin cofactor to cardiolipin

After 2.5 μg/50 μl/well each of an ethanol solution of cardiolipin was added to each well of a 96 well microtiter plate, drying was performed under reduced pressure followed by reacting in 1% pBSA-containing PBS for an hour. Thereafter, the plate was washed 3 times with PBS (200 μl) containing 0.05% Tween 20. Then, 0 to 32 μg/ml of biotinylated anticardiolipin cofactor (100 μl) indicated in FIG. 20 was reacted with this cardiolipin-bound plate for 30 minutes at room temperature. After washing 3 times, avidin labeled peroxidase was reacted therewith at room temperature for 30 minutes. After washing further 3 times, aqueous solution containing 100 μl of 0.3 mM TMBZ and 0.003% hydrogen peroxide was added to the mixture. After reacting at room temperature for 10 minutes, the reaction was terminated by adding 100 μl of 2N sulfuric acid to the reaction solution. By measuring absorbance of the reaction solution, the anticardiolipin cofactor bound to the solid phase cardiolipin was quantitatively determined.

Figure 20:
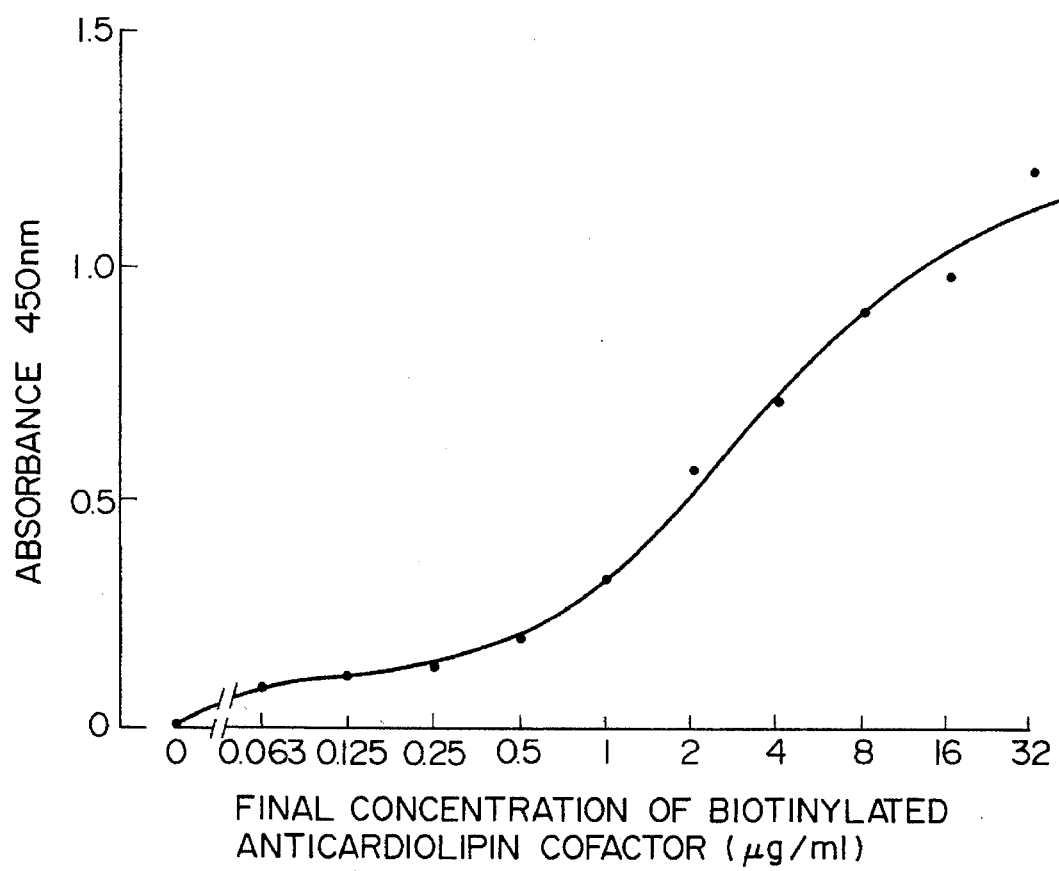
FIG. 20 is a graph showing binding ability of concentration-dependent biotinylated anticardiolipin cofactor on cardiolipin solid phase plate.

As shown in FIG. 20, the biotinylated anticardiolipin cofactor shows its binding ability to the solid phase cardiolipin dependently on its concentration.

Figure 21:
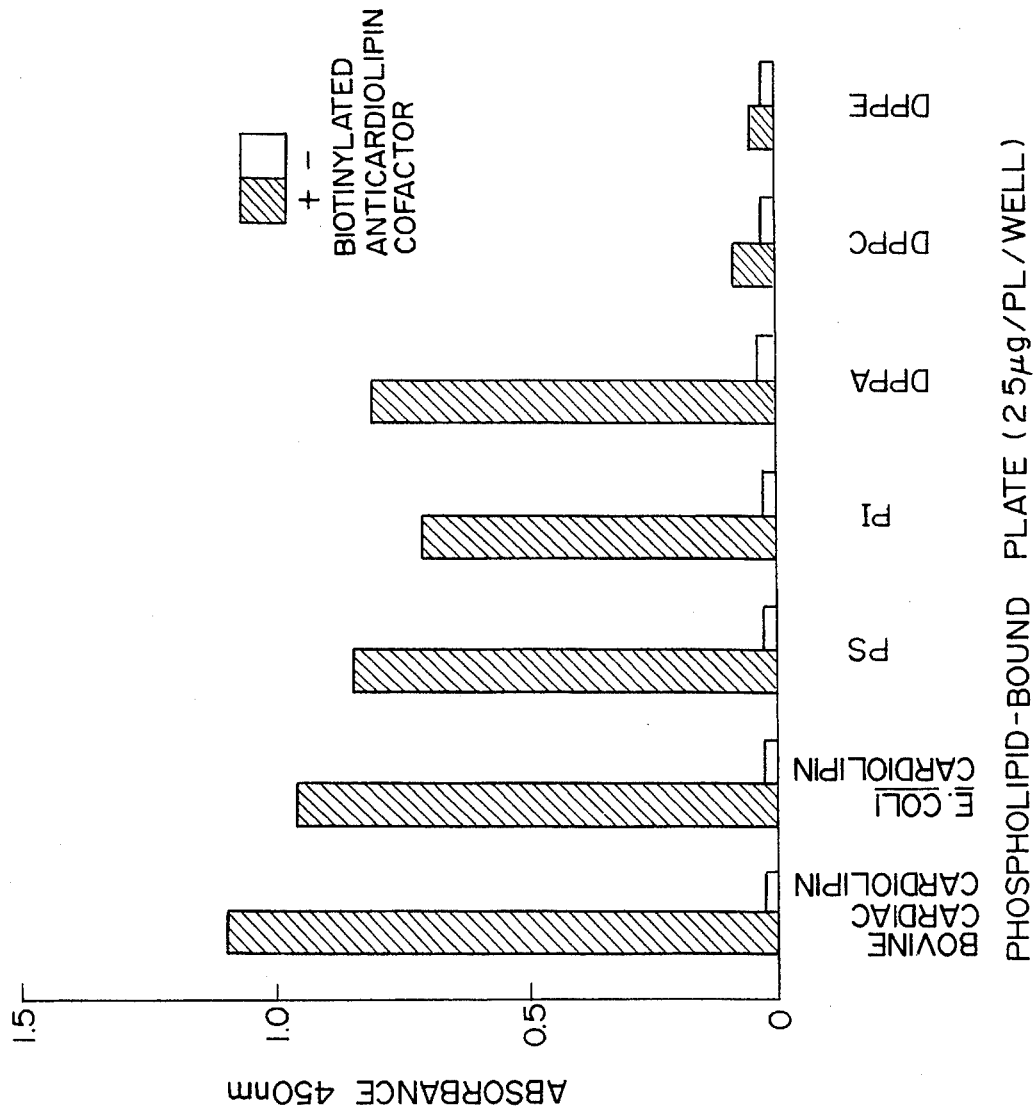
FIG. 21 is a graph showing binding specificity of anticardiolipin cofactor to phospholipids.

(3) Binding specificity of the biotinylated anticardiolipin cofactor to various phospholipids Using avidin labeled peroxidase, binding specificity of the biotinylated anticardiolipin cofactor to the phospholipids was examined on the plate, onto which 2.5 μg/50 μl/well each of various phospholipids [namely, cardiolipin, phosphatidylserine (PS), phosphatidylinositol (PI), dipalmitoylphosphatidic acid (DPPA), dipalmitoyl phosphatidylcholine (DPPC) and dipalmitoylphosphatidylethanolamine (DPPE)] had been bound. As shown in FIG. 21, the binding of the anticardiolipin cofactor was specific to the acidic phospholipids (cardiolipin, PS, PI and DPPA) having negative charge.

Figure 22:
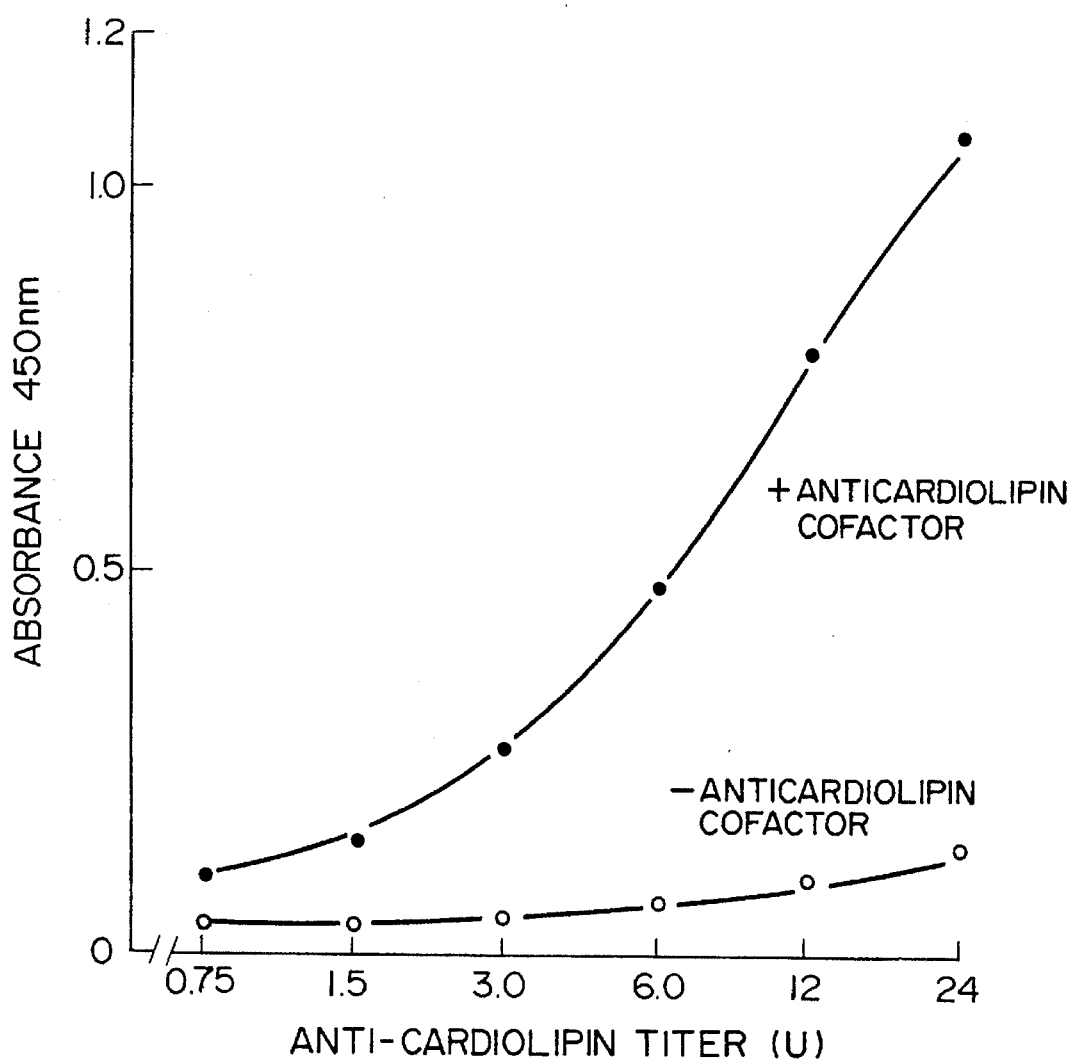
FIG. 22 is a graph showing dependency of anticardiolipin cofactor on anti-cardiolipin antibody (As antibody) binding to the solid phase.

(4) Dependency of the anticardiolipin cofactor on anti-cardiolipin antibody binding in the reaction system According to ELISA similar to (2) described above, the anticardiolipin cofactor (2 μg/well) was added to the reaction system of anti-cardiolipin antibody (As serum) specifically present in the antiphospholipid syndrome with cardiolipin bound to the solid phase to examine dependency of the anticardiolipin cofactor on the reaction between anti-cardiolipin antibody and the solid phase cardiolipin. As shown in FIG. 22, anti-cardiolipin antibody was reacted dependently on the anticardiolipin cofactor added.

(5) Species specificity of the anticardiolipin cofactor

Figure 23:
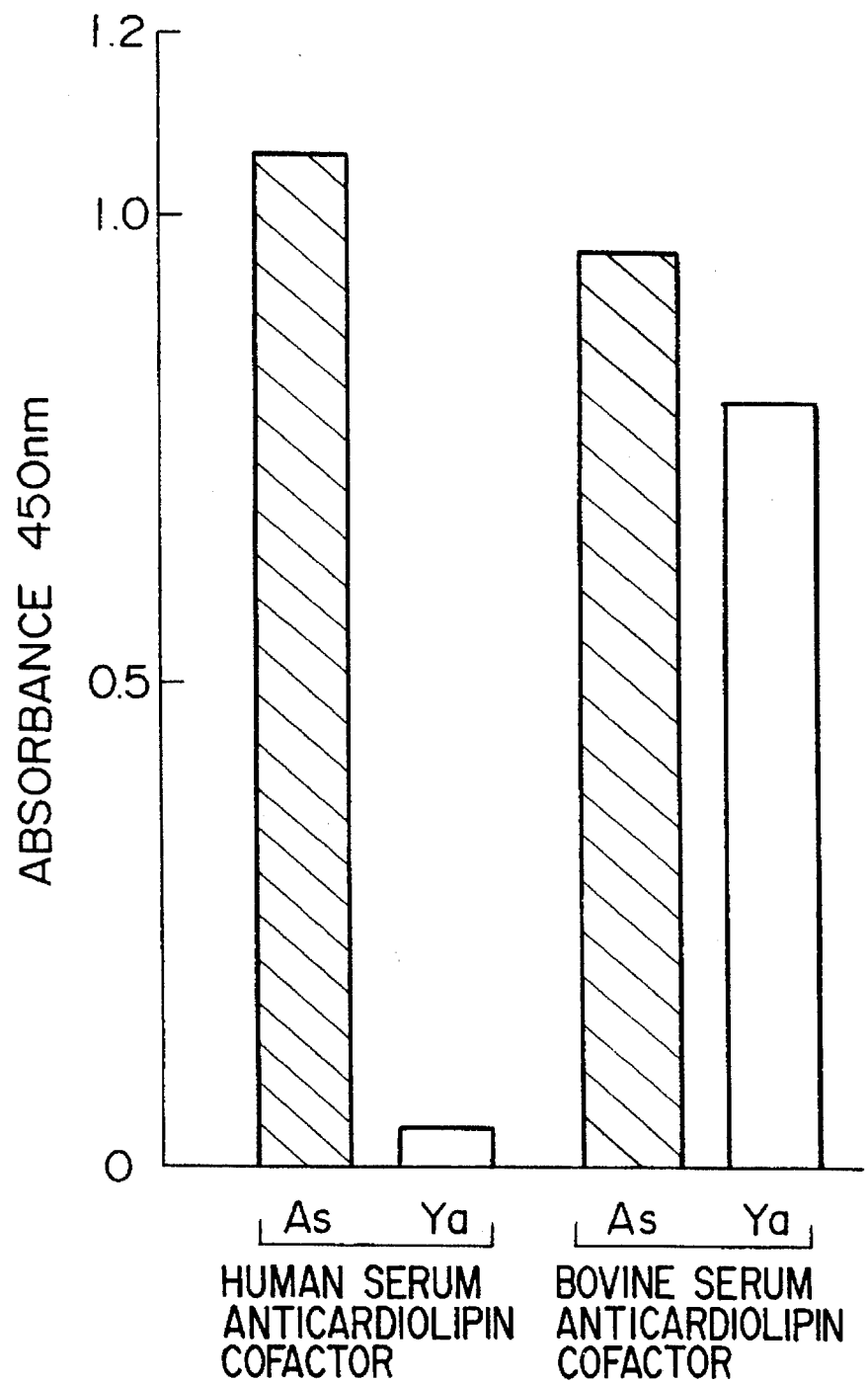
FIG. 23 is a graph showing species specificity of anticardiolipin cofactor in the detection system of anti-cardiolipin antibody.

The activity of anticardiolipin cofactors from different species (derived from human and bovine) were evaluated by ELISA similar to (2) described above. When the bovine-derived cofactor was used, the reactivities of anti-cardiolipin antibodies from autoimmune disease (As serum) and infectious disease (Ya serum) were both enhanced. However, when the human-derived cofactor was used, the reactivity of the antibody from autoimmune diseases (As antibody) was selectively enhanced (FIG. 23).

Example 11

Collection of the fraction from human sera obtained from normal subjects
(1) Collection of the fraction by DEAE-cellulose column chromatography Human sera (1 ml) from normal subjects which had been dialyzed against 14 mM sodium phosphate buffer (pH 7.4) (hereafter PB 7.4) overnight were subjected to DEAE-Sepharose column (10 ml, 1.0 Ø×13 cm, DE-52, manufactured by Whatmann Co.) which had been previously equilibrated with PB 7.4. The effluent was recovered by 1 ml each. Using 25 μl of each fraction, both the activity of enhancing the reactivity between anti-cardiolipin antibody specifically appeared in sera (As) from patients with antiphospholipid syndrome and cardiolipin on the solid phase, and the activity of preventing the reactivity between anti-cardiolipin antibody present in sera (Sy) from patients with syphilis and cardiolipin on the solid phase were determined in a manner almost similar to the method described in Reference Example and Example 10, Method (B).

Figure 24:
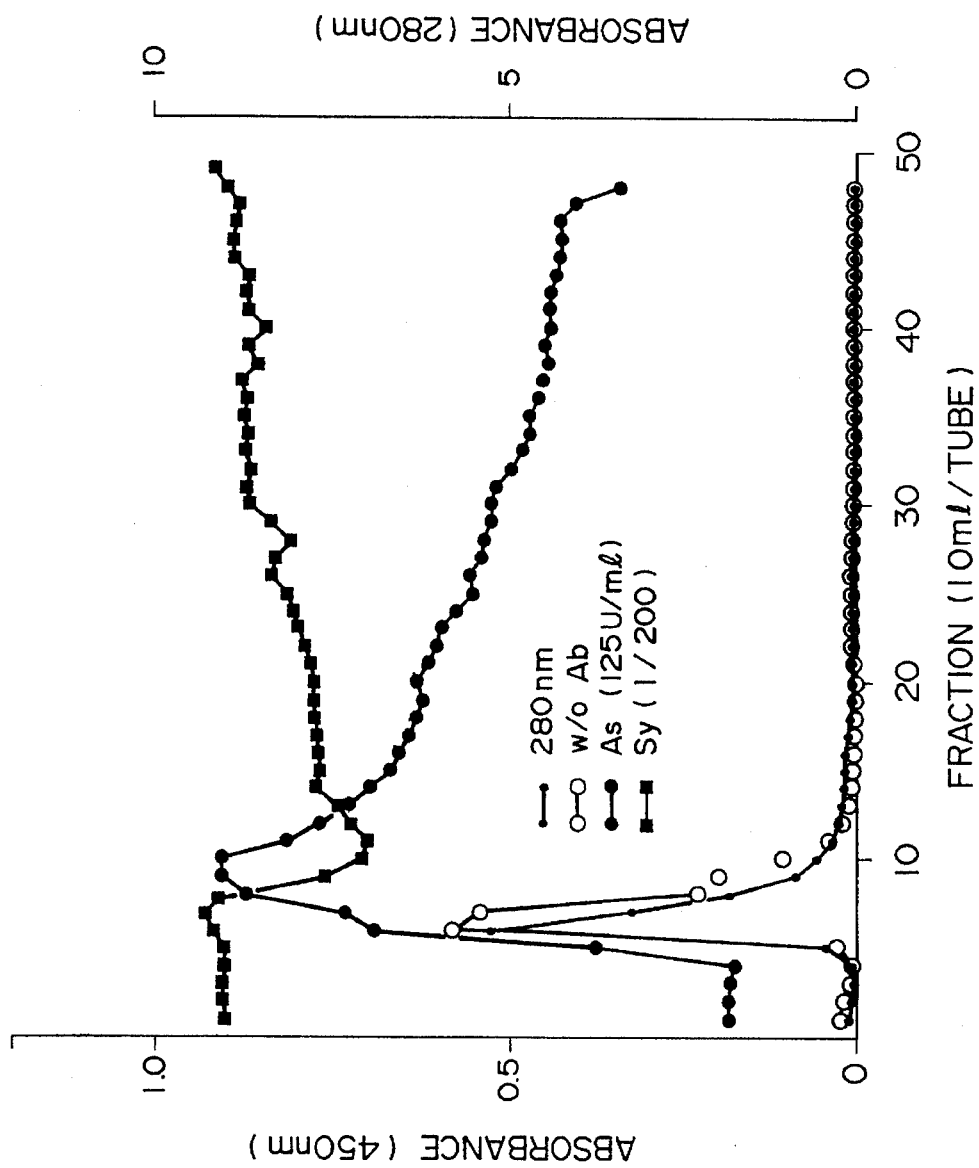
FIG. 24 shows a chromatogram of serum from normal subjects by DEAE-cellulose column chromatography.

The results are shown in FIG. 24.

(2) Collection of the fraction by heparin-Sepharose column chromatography

Human sera (1 ml) from normal subjects which had been dialyzed overnight to 10 mM sodium phosphate buffer (pH 7.4) containing 50 mM sodium chloride was adsorbed onto heparin-Sepharose column (6 ml, 1.0 Ø×8 cm, manufactured by Pharmacia) which had been previously equilibrated with the same buffer. After the column was thoroughly washed with the same buffer, elution was performed by density gradient of sodium chloride concentration from 50 mM to 1M. Using 15 μl of each fraction, both the activity of enhancing the reactivity between anti-cardiolipin antibody specifically appeared in sera (As) from patients with antiphospholipid syndrome and cardiolipin on the solid phase, and the activity of preventing the reactivity between anti-cardiolipin antibody present in sera (Sy) from patients with syphilis and cardiolipin on the solid phase were determined in a manner almost similar to the method described in Reference Example and Example 10, Method (B).

Figure 25:
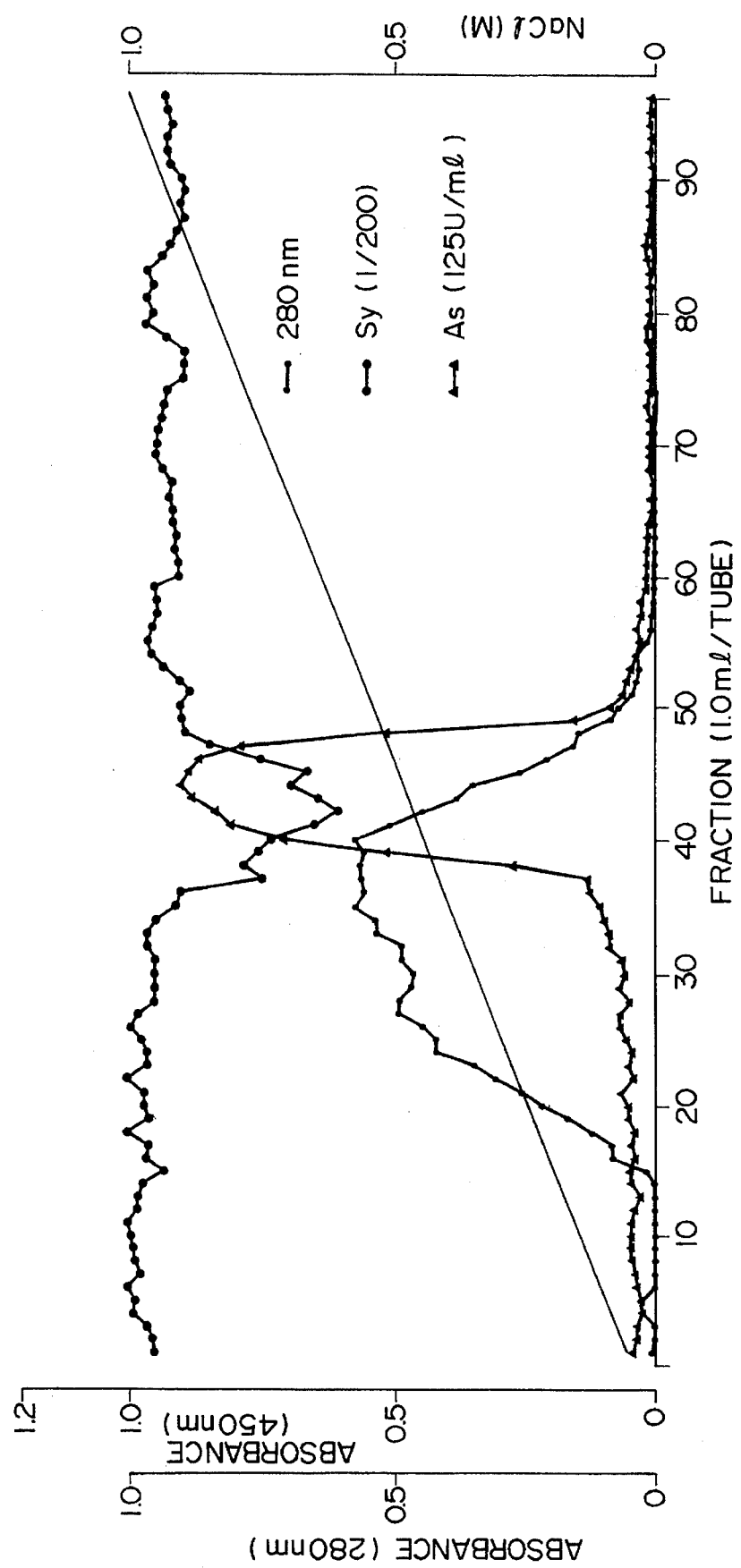
FIG. 25 shows a chromatogram of serum from normal subjects by heparin-Sepharose column chromatography.

The results are shown in FIG. 25.

(3) Collection of the fraction by cardiolipin-polyacrylamide gel column chromatography i) Preparation of cardiolipin-polyacrylamide gel column Bovine heart-derived cardiolipin (5 μmoles), cholesterol (5 μmoles) and dicetyl phosphate (0.5 μmoles) were charged in a pear type flask and dried film-like under reduced pressure. Furthermore, 500 μl of ethanol was added thereto and the flask was warmed to about 60° C. to dispense the lipid. Next, 5 ml of a solution of 15% acrylamide and 5% N,N'-methylenebisacrylamide was added to the solution. The mixture was vigorously stirred with a vortex mixer and, 100 μl of ammonium persulfate (100 mg/ml) and 2 μl of TEMED were added thereto to cause polymerization. The polymerized gel was homogenized. The homogenate was packed in a column (1.0 Ø×3 cm) and the gel was thoroughly washed and equilibrated with 10 mM sodium phosphate buffer (pH 7.4) containing 50 mM sodium chloride.

ii) Affinity column chromotography

After 1 ml of human sera from normal subjects which had been dialyzed overnight to 10 mM sodium phosphate buffer (pH 7.4) containing 50 mM sodium chloride was passed through the column, the column was thoroughly washed with the same buffer and the proteins adsorbed to the column were eluted with 10 mM sodium phosphate buffer (pH 7.4) containing 1.0M sodium chloride. Using 15 μl of each fraction, both the activity of enhancing the reactivity between anti-cardiolipin antibody specifically appeared in sera (As) from patients with antiphospholipid syndrome and cardiolipin on the solid phase, and the activity of preventing the reactivity between anti-cardiolipin antibody present in sera (Sy) from patients with syphilis and cardiolipin on the solid phase were determined in a manner almost similar to the method described in Reference Example and Example 10, Method (B).

Figure 26:
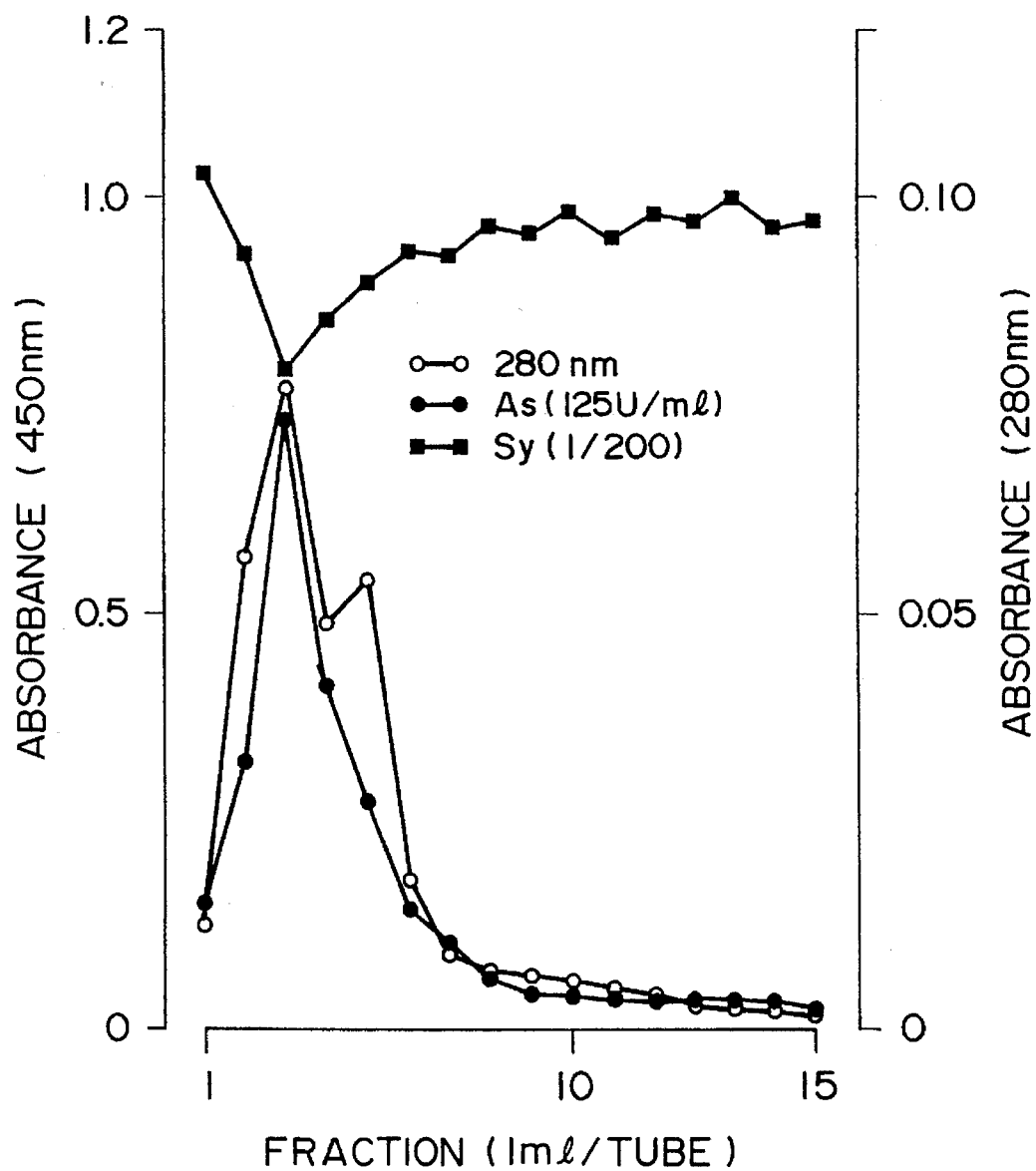
FIG. 26 shows a chromatogram of serum from normal subjects by cardiolipin-polyacrylamide gel column chromatography.

The results are shown in FIG. 26.

As stated above, the fraction of the present invention could be obtained from human serum from normal subjects, using DEAE-cellulose column chromotography, heparin-Sepharose column chromotography or cardiolipin-polyacrylamide gel column chromotography.

Example 12

Activity of the anticardiolipin cofactor

Expression of the activity (As ↑ activity) of enhancing the reactivity between anti-cardiolipin antibody specifically appeared in sera (As) from patients with antiphospholipid syndrome and cardiolipin, and the activity (Sy ↓ activity) of preventing the reactivity between anti-cardiolipin antibody present in sera (Sy) from patients with syphilis and cardiolipin was examined.

The solid phase-cardiolipin plate was washed with PBS containing Tween 20. Thereafter, the plate used for Groups 3 and 4 in the sera groups shown in Table 6 were treated for 30 minutes with the cofactor (10 μg/ml) obtained in Example 10 (3). The plate used for control group was treated with the buffer not containing the cofactor. After the treatment, the plate was washed 3 times with PBS containing Tween 20 and then reacted with As serum (diluted to a concentration of 1/400-fold, 125 U/ml) and Sy serum (diluted to a concentration of 1/200-fold) at room temperature for 30 minutes in the presence (Groups 2 and 4) of the cofactor (10 μg/ml) or in the absence (Groups 1 and 3) of the cofactor. Subsequent procedures were similar to those in Reference Example and Example 10 (B).

As shown in Table 6, for expressing the As ↑ activity, the cofactor should be present in the pretreatment of the plate, be present in the reaction system with the antibody or is present both in the pretreatment and in the reaction system as described above. In order to express the Sy ↓ activity, the cofactor may be present in the pretreatment of the plate but should be present in the reaction system with the antibody.

TABLE 6

| Group | Pretreated with Cofactor | Incubation of Patient's Sera with Cofactor (As or Sy) | Absorbance (450 nm) |
|---|---|---|---|
| As |   |   |   |
| Group 1 | − | − | 0.102 |
| Group 2 | − | + | 1.051 |
| Group 3 | + | − | 0.826 |
| Group 4 | + | + | 1.102 |
| Sy |   |   |   |
| Group 1 | − | − | 1.106 |

TABLE 6-continued

| Group | Pretreated with Cofactor | Incubation of Patient's Sera with Cofactor (As or Sy) | Absorbance (450 nm) |
|---|---|---|---|
| Group 2 | − | + | 0.710 |
| Group 3 | + | − | 1.125 |
| Group 4 | + | + | 0.850 |

Example 13

Influence of purified bovine serum albumin on the activity (As ↑ activity) of enhancing the reactivity between anti-cardiolipin antibody specifically appeared in sera (As) from patients with antiphospholipid syndrome and cardiolipin, and the activity (Sy ↓ activity) of preventing the reactivity between anti-cardiolipin antibody present in sera (Sy) from patients with syphilis and cardiolipin was examined according to the method almost similar to that described in Reference Example and Example 10, Method (B).

When bovine serum albumin highly purified, containing no lipid (pBSA) and the purified cofactor [cofactor obtained in Example 10 (3)] were used in this determination, the Sy ↓ activity decreases dependently on the concentration of pBSA in the reaction solution (FIG. 27). This is believed to be because the Sy ↓ activity expression site on the cofactor molecule would be blocked by the purified albumin (pBSA). Therefore, it is desired to use BSA in a concentration of 0 to 5%, preferably 0 to 1%.

Example 14

Determination of amino acid sequence in the cofactor

The cofactor obtained by the method described in Example 10 (3) was further subjected to cardiolipin-polyacrylamide gel column chromatography used in Example 11 (3) to adsorb the cofactor on the gel. Then, the cofactor was eluted with 1M sodium chloride to purify the cofactor. The N-terminal amino acid sequence of the cofactor [the two subtypes identified in Example 10 (6) were contained in the cofactor] was determined. That is, 30 μl (300 pmols) of a sample solution was adsorbed onto PVDF membrane (polyvinylidene difluoride; trademark, IMOBILON, manufactured by Millipore Co.). After washing with 60% methanol, analysis was made with a vapour phase protein sequencer (Model PSQ-1, manufactured by Shimadzu Seisakusho Ltd.). By the foregoing procedures, the sequence of 5 amino acids from the N-terminus of the cofactor was determined.

```
              1           5
Result:  NH2—Gly—Arg—Thr—X—Pro—Lys—Pro
              (X is assumed to be Cys or His.)
```

Industrial Applicability

According to the present invention, a method for distinguishably and independently determining the anti-phospholipid antibody of antiphospholipid syndrome origin and the anti-phospholipid antibody of infectious disease origin, which could not be sufficiently distinguished from each other in the prior art, has been established with good reproducibility, by using the carrier for binding of an antiphospholipid antibody treated with the surfactant alone, combination of the surfactant and purified serum albumin or treated with them further in combination with the blood component(s) of the present invention, and/or adding the blood component(s) of the present invention to the reaction solution in the first antigen-antibody reaction (primary reaction). By applying the method of the present invention, diagnosis of antiphospholipid syndrome can be made extremely accurately.

In addition, the blood component(s) of the present invention have (has) the activity of enhancing the binding ability of the antibody specifically present in the patient with the antiphospholipid syndrome to phospholipids and reducing the binding ability of the anti-phospholipid antibody of infectious disease origin to phospholipids. Accordingly, by using these sera or plasma or their fraction or protein in the fraction for immunoassay of the antibody specifically present in the patient with the antiphospholipid syndrome, diagnosis of the antiphospholipid syndrome can be made accurately. At the same time, the respective anti-phospholipid antibodies in the antiphospholipid syndrome and infectious diseases can be detected distinguishably from each other.

What is claimed is:

1. A method for differentially detecting an antiphospholipid antibody derived from antiphospholipid syndrome and an antiphospholipid antibody derived from infectious disease which comprises contacting a phospholipid-bound carrier for binding of an antiphospholipid antibody with a sample solution, wherein the phospholipid-bound carrier for binding of an antiphospholipid antibody is contacted with the sample solution both in the presence and in the absence of a protein, which is obtained from human serum or plasma, has a function of enhancing the binding of an antibody specifically present in antiphospholipid syndrome with phospholipid and has the following physicochemical properties:

a) its molecular weight is about 50,000±2,000 when determined by SDS-polyacrylamide gel electrophoresis and its isoelectric point is about 6.60±0.4; and b) the protein is capable of binding to phospholipid, and comparing the extent of binding between the antibody and bound phospholipid in the presence and in the absence of the protein, thereby to differentially detect the antiphospholipid antibody derived from antiphospholipid syndrome and the antiphospholipid antibody derived from infectious disease.

2. The method according to claim 1, wherein said phospholipid is immobilized on a microtiter plate.

3. The method according to claim 1, wherein said protein is provided in the form of a serum or plasma containing the protein or fraction thereof.

4. The method according to claim 1, wherein said protein is provided in the form of a sample dilution containing the protein.

5. The method according to claim 1, wherein said sample solution is a human blood or fraction thereof.

6. The method according to claim 1, wherein said phospholipid is cardiolipin.

7. The method according to claim 1, wherein said antiphospholipid antibody is an anti-cardiolipin antibody.

* * * * *